US008883755B2

(12) United States Patent
Palladino et al.

(10) Patent No.: US 8,883,755 B2
(45) Date of Patent: Nov. 11, 2014

(54) MITOCHONDRIAL TARGETED RNA EXPRESSION SYSTEM AND USE THEREOF

(71) Applicant: University of Pittsburgh-Of the Commonwealth System of Higher Education, Pittsburgh, PA (US)

(72) Inventors: Michael J. Palladino, Pittsburgh, PA (US); Alicia M. Palladino, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/860,156

(22) Filed: Apr. 10, 2013

(65) Prior Publication Data

US 2013/0274314 A1    Oct. 17, 2013

Related U.S. Application Data

(60) Provisional application No. 61/622,649, filed on Apr. 11, 2012, provisional application No. 61/717,741, filed on Oct. 24, 2012.

(51) Int. Cl.

| | |
|---|---|
| *C12N 15/11* | (2006.01) |
| *C12N 15/87* | (2006.01) |
| *A01K 67/033* | (2006.01) |
| *C12N 15/85* | (2006.01) |
| *A61K 38/46* | (2006.01) |
| *C12N 15/113* | (2010.01) |
| *A61K 48/00* | (2006.01) |

(52) U.S. Cl.
CPC ............ *C12N 15/85* (2013.01); *A01K 67/0339* (2013.01); *C12N 15/8509* (2013.01); *A01K 2227/706* (2013.01); *A61K 38/46* (2013.01); *C12N 2840/00* (2013.01); *C12N 15/1137* (2013.01); *C12N 2320/32* (2013.01); *C12N 2310/11* (2013.01); *C12Y 306/03014* (2013.01); *A61K 48/005* (2013.01); *C07K 2319/07* (2013.01)
USPC ......................................... 514/44 A; 435/466

(58) Field of Classification Search
None
See application file for complete search history.

(56) References Cited

U.S. PATENT DOCUMENTS

| | | | |
|---|---|---|---|
| 2004/0072774 A1* | 4/2004 | Manfredi et al. | ............... 514/44 |
| 2006/0183231 A1* | 8/2006 | Pachuk et al. | ................. 435/456 |

FOREIGN PATENT DOCUMENTS

WO    WO 9838335 A1 *  9/1998

OTHER PUBLICATIONS

Smirnov et al, Two distinct structural elements of 5S rRNA are needed for its import into human mitochondria, 2008, RNA, 14: 749-759.*
Preiser et al, In Vitro Processing of *Drosophila melanogaster* 5 S Ribosomal RNA, 1991, Journal of Biological Chemistry, vol. 266, 12: 7509-7516.*
Shoubridge, Cytochrome c Oxidase Deficiency, 2001, American Journal of Medical Genetics, 106:46-52.*
Macino et al, Use of the UGA terminator as a tryptophan codon in yeast mitochondria, 1979, PNAS, vol. 76, 8: 3784-3785.*
Lytle et al, Target mRNAs are repressed as efficiently by microRNA-binding sites in the 5' UTR as in the 3' UTR, 2007, PNAS, vol. 104, 23: 9667-9672.*
Gunnery et al., "Functional mRNA can be Generated by RNA Polymerase III," *Mol. Cell. Biol.*, vol. 15(7):3597-3607, 1995.
Keeney et al., "Mitochondrial Gene Therapy Augments Mitochondrial Physiology in a Parkinson's Disease Cell Model," *Hum. Gene Ther.*, vol. 20:897-907, 2009.
Manfredi et al., "Rescue of a deficiency in ATP synthesis by transfer of MTATP6, a mitochondrial DNA-encoded gene, to the nucleus," *Nat. Genet.*, vol. 30(4):394-399, 2002.
Orioli et al., "Widespread Occurrence of Non-Canonical Transcription Termination by Human RNA Polymerase III," *Nucl. Acids Res.*, vol. 39(13):5499-5512, 2011.
Schramm et al., "Recruitment of RNA Polymerase III to its Target Promoters," *Genes Dev.*, vol. 16:2593-2620, 2002.
Wang et al., "PNPASE Regulates RNA Import into Mitochondria," *Cell*, vol. 142:456-467, 2010.
Wang et al., "Correcting Human Mitochondrial Mutations with Targeted RNA Import," *Proc. Natl. Acad. Sci. USA*, vol. 109(13):4840-4845, 2012.

* cited by examiner

*Primary Examiner* — Tracy Vivlemore
*Assistant Examiner* — Kate Poliakova-Georgantas
(74) *Attorney, Agent, or Firm* — Klarquist Sparkman, LLP

(57) ABSTRACT

Described herein is a mitochondrial-targeted RNA expression system (mtTRES) for delivery of RNA molecules to mitochondria. mtTRES vectors generate RNAs in vivo that are un-capped, non-polyadenylated, and actively directed to mitochondria. The disclosed vectors are capable of delivering either non-coding RNA molecules or RNA molecules encoding a protein of interest to the mitochondria. In particular, the disclosed vectors include (1) an RNAPIII initiation (promoter) sequence, (2) a non-coding leader sequence (NCL), (3) a mitochondrial translation initiation sequence and an ORF encoding a protein of interest, or a sequence encoding a non-coding RNA, and (4) an RNAPIII termination sequence.

21 Claims, 10 Drawing Sheets

FIG. 1A
FIG. 1B
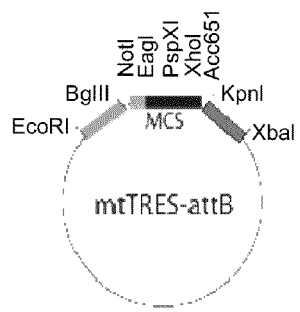
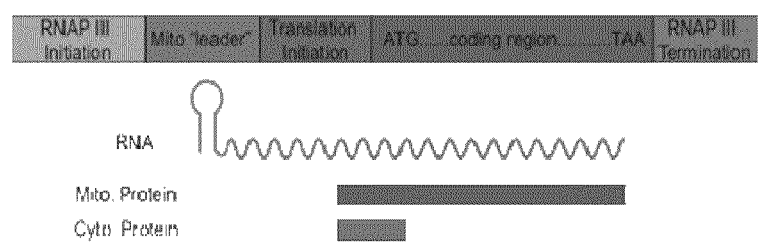
FIG. 1C
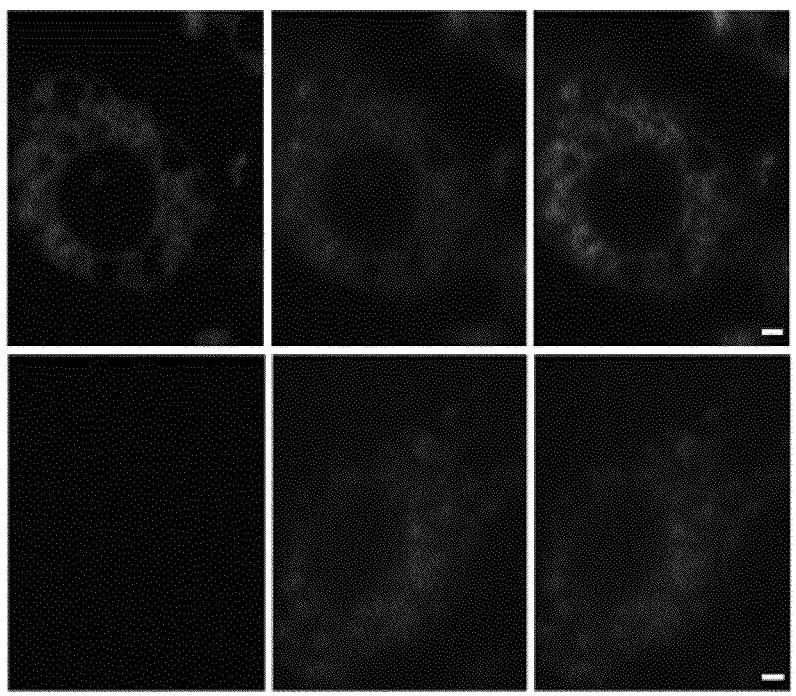

SEQUENCE LISTING

<160> NUMBER OF SEQ ID NOS: 50

<210> SEQ ID NO 1
<211> LENGTH: 120
<212> TYPE: RNA
<213> ORGANISM: Artificial Sequence
<220> FEATURE:
<223> OTHER INFORMATION: Synthetic polynucleotide

<400> SEQUENCE: 1
gccaacgacc auaccacgcu gaauacaucg guucucgucc gaucaccgaa auuaagcagc     60
gucgggcgcg guuaguacuu agauggggga ccgcuuggga acaccgcgug uuguuggccu    120

<210> SEQ ID NO 2
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 2

```
gccaacgacc ataccacgct gaatacatcg gttctcgtcc gatcaccgaa attaagcagc    60
gtcgggcgcg gttagtactt agatggggga ccgcttggga acaccgcgtg ttgttggcct   120
```

<210> SEQ ID NO 3
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 3

```
agaagcguau cccgcugagc                                                 20
```

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4

```
agaagcgtat cccgctgagc                                                 20
```

<210> SEQ ID NO 5
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 5

```
ucucccugag cuucagggag                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6

```
tctccctgag cttcagggag                                                 20
```

<210> SEQ ID NO 7
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 7

```
uuaaauucaa uaaauugaaa                                                 20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8

```
ttaaattcaa taaattgaaa                                                 20
```

<210> SEQ ID NO 9
<211> LENGTH: 70

```
<212> TYPE: DNA
<213> ORGANISM: Artificial Sequence
<220> FEATURE:
<223> OTHER INFORMATION: Synthetic polynucleotide

<400> SEQUENCE: 9
cagtctattt cagtctatgg gcataactga atatcagagt ataaggacac tgtttagccc    60
ctcgactttc                                                          70

<210> SEQ ID NO 10
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 10
cccagtggaa agacgcgcag gcaaaacgca ccacgtgacg gagcgtgacc gcgcgccgag    60
cgcgcgccaa ggtcgggcag gaagagggcc tatttcccat gattccttca tatttgcata   120
tacgatacaa ggctgttaga gagataatta gaattaattt gactgtaaac acaaagatat   180
tagtacaaaa tacgtgacgt agaaagtaat aatttcttgg gtagtttgca gttttaaaat   240
tatgttttaa aatggactat catatgctta ccgtaacttg aaagtatttc gatttcttgg   300
gtttatatat cttgtggaaa ggacgcg                                      327

<210> SEQ ID NO 11
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 11
cgtccacaac tttttgctgc ctgctgcctg ctgcctgctg cc                       42

<210> SEQ ID NO 12
<211> LENGTH: 695
<212> TYPE: RNA
<213> ORGANISM: Artificial Sequence
<220> FEATURE:
<223> OTHER INFORMATION: Synthetic polynucleotide

<400> SEQUENCE: 12
uuaaauucaa uaaauugaaa augauaacaa auuuauucuc uguauucgac cccuuagcua    60
ucuuuaauuu cucacuuaau ugauuaagaa cauucuaggg acucuaaaua auuccuagga   120
ucuauugauu aauaccuucu cguuacaaua uuauaugaaa uucaaucuua uuaacucuuc   180
auaaagaauu uaaaacuuua uuaggaccau caggucauaa uggaucuacu uucaucuuua   240
uuucuuuauu cucauuaauc uauuuaaua auucauagg auuauuucca uauaucuuua    300
caagaacaag acauuuaacu uuaacuuuau cuuuagcuuu accuuauga uuauguuuca    360 uauuauaugg augaauuaau cauacacaac auauauuugc ucauuuaguu ccucaaggaa   420
cacccgcuau ucuuauaccu uucuagauau guauugaaac uauuagaaau auuauucgac   480
cuggaacauu agcuguucga uuaacugcua auauaauugc uggacauuua uuauuaacuc   540
ucuuaggaaa uacaggaucu ucuauaucuu auauauuaau aacauucuua uuaauagcuc   600
aaauugcuuu auuaguauua gaaucagcug uagcuauaau ucaaucuuau uguuugcug    660 uauuaagaac uuuauauucu agagaaguaa auuaa                              695
```

<210> SEQ ID NO 13
<211> LENGTH: 695
<212> TYPE: DNA
<213> ORGANISM: Artificial Sequence
<220> FEATURE:
<223> OTHER INFORMATION: Synthetic polynucleotide

<400> SEQUENCE: 13

```
ttaaattcaa taaattgaaa atgataacaa atttattctc tgtattcgac cccttagcta      60
tctttaattt ctcacttaat tgattaagaa cattcttagg actcttaata attcctagga     120
tctattgatt aataccttct cgttacaata ttatatgaaa ttcaatctta ttaactcttc     180
ataaagaatt taaaacttta ttaggaccat caggtcataa tggatctact ttcatcttta     240
tttctttatt ctcattaatc ttatttaata atttcatagg attatttcca tatatcttta     300
caagaacaag acatttaact ttaactttat ctttagcttt acctttatga ttatgtttca     360
tattatatgg atgaattaat catacacaac atatatttgc tcatttagtt cctcaaggaa     420
cacccgctat tcttatacct ttcatagtat gtattgaaac tattagaaat attattcgac     480
ctggaacatt agctgttcga ttaactgcta atataattgc tggacattta ttattaactc     540
tcttaggaaa tacaggatct tctatatctt atatattaat aacattctta ttaatagctc     600
aaattgcttt attagtatta gaatcagctg tagctataat tcaatcttat gtgtttgctg     660
tattaagaac tttatattct agagaagtaa attaa                                695
```

<210> SEQ ID NO 14
<211> LENGTH: 740
<212> TYPE: RNA
<213> ORGANISM: Artificial Sequence
<220> FEATURE:
<223> OTHER INFORMATION: Synthetic polynucleotide

<400> SEQUENCE: 14

```
uuaaauucaa uaaauugaaa auggugagca agggcgagga gcuguucacc ggugugguge      60 ccauccuggu cgagcuggac ggcgacguaa acggccacaa guucagcgug uccggcgagg     120
gcgagggcga ugccaccuac ggcaagcuga cccugaaguu caucugcacc accggcaagc     180
ugcccgugcc cugacccacc cucgugacca cccugaccua cggcgugcag ugcuucagcc     240
gcuaccccga ccacaugaag cagcacgacu ucuucaaguc cgccaugccc gaaggcuacg     300
uccaggagcg caccaucuuc uucaaggacg acggcaacua caagacccgc gccgagguga     360
aguucgaggg cgacacccug gugaaccgca ucgagcugaa gggcaucgac uucaaggagg     420
acggcaacau ccuggggcac aagcuggagu acaacuacaa cagccacaac gucuauauca     480
uggccgacaa gcagaagaac ggcaucaagg ugaacuucaa gauccgccac aacaucgagg     540
acggcagcgu gcagcucgcc gaccacuacc agcagaacac ccccaucggc gacggccccg     600
ugcugcugcc cgacaaccac uaccugagca cccaguccgc ccugagcaaa gaccccaacg     660
agaagcgcga ucacaugguc cugcuggagu ucgugaccgc cgccgggauc acucucggca     720
uggacgagcu guacaaguaa                                                 740
```

<210> SEQ ID NO 15
<211> LENGTH: 740
<212> TYPE: DNA
<213> ORGANISM: Artificial Sequence
<220> FEATURE:
<223> OTHER INFORMATION: Synthetic polynucleotide

<400> SEQUENCE: 15

```
ttaaattcaa taaattgaaa atggtgagca agggcgagga gctgttcacc ggtgtggtgc    60
ccatcctggt cgagctggac ggcgacgtaa acggccacaa gttcagcgtg tccggcgagg   120
gcgagggcga tgccacctac ggcaagctga ccctgaagtt catctgcacc accggcaagc   180
tgcccgtgcc ctgacccacc ctcgtgacca ccctgaccta cggcgtgcag tgcttcagcc   240
gctaccccga ccacatgaag cagcacgact tcttcaagtc cgccatgccc gaaggctacg   300
tccaggagcg caccatcttc ttcaaggacg acggcaacta caagacccgc gccgaggtga   360
agttcgaggg cgacaccctg gtgaaccgca tcgagctgaa gggcatcgac ttcaaggagg   420
acggcaacat cctggggcac aagctggagt acaactacaa cagccacaac gtctatatca   480
tggccgacaa gcagaagaac ggcatcaagg tgaacttcaa gatccgccac aacatcgagg   540
acggcagcgt gcagctcgcc gaccactacc agcagaacac ccccatcggc gacggccccg   600
tgctgctgcc cgacaaccac tacctgagca cccagtccgc cctgagcaaa gaccccaacg   660
agaagcgcga tcacatggtc ctgctggagt tcgtgaccgc cgccgggatc actctcggca   720
tggacgagct gtacaagtaa                                               740

<210> SEQ ID NO 16
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 16 atacccatt tataaaggtt ataatccttt tcttttaat t                          41

<210> SEQ ID NO 17
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 17
acaatctatc gcctaaactt cagccactta atcaataatc g                        41

<210> SEQ ID NO 18
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 18
ctctatatat aaagtatttt acttttatta gaaataaat g                         41

<210> SEQ ID NO 19
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 19
atgtcaaact aaaattatta aataattaat atttttttaat t                       41

<210> SEQ ID NO 20
<211> LENGTH: 42
<212> TYPE: DNA
```

<213> ORGANISM: Artificial Sequence
<220> FEATURE:
<223> OTHER INFORMATION: Synthetic polynucleotide

<400> SEQUENCE: 20
gaattaaaaa aatatcaact taaattcaat aaattgaaaa tg          42

<210> SEQ ID NO 21
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 21
gctgtattaa gaactttata ttctagagaa gtaaattaat g          41

<210> SEQ ID NO 22
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 22
cttccaatca taaggtctat taattaatag tatagataat t          41

<210> SEQ ID NO 23
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 23
ttgtggtgtt agtgatatga aaatattcat tttaaatcat g          41

<210> SEQ ID NO 24
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 24
catggtaatg attattttca atcttttaga attatataat g          41

<210> SEQ ID NO 25
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 25
tttacaagac caatgttttt attaaactat taaaactaat g          41

<210> SEQ ID NO 26
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 26
tcttgaagtt ttaaagaaa taatcttatt tttgatttat t           41

<210> SEQ ID NO 27
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 27
aattatttaa aggacctatt cgaataatat cttaattaat g                         41

<210> SEQ ID NO 28
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 28
ttagaattta tatatgtgat ttttattaca aatagtactt g                         41

<210> SEQ ID NO 29
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 29
wtttcaawtw aaaatttttt aaatttwtaw wttaattaat g                         41

<210> SEQ ID NO 30
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 30
gtcagaggtt caattcctct tcttaacaac atacc                                35

<210> SEQ ID NO 31
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 31
gaaaatgttg gttataccct tcccgtacta attaa                                35

<210> SEQ ID NO 32
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 32
tcactcagcc attttacctc acccccactg atgtt                                35

<210> SEQ ID NO 33
<211> LENGTH: 35
<212> TYPE: DNA
<213> ORGANISM: Artificial Sequence
<220> FEATURE:

<223> OTHER INFORMATION: Synthetic polynucleotide

<400> SEQUENCE: 33
taaattatag gctaaatcct atatatctta atggc                                    35

<210> SEQ ID NO 34
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 34
ttaagagaac caacacctct ttacagtgaa atgcc                                    35

<210> SEQ ID NO 35
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 35
aaaaaattat aacaaaccct gagaaccaaa atgaa                                    35

<210> SEQ ID NO 36
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 36
agtaagcctc tacctgcacg acaacacata atgac                                    35

<210> SEQ ID NO 37
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 37
actagttttg acaacattca aaaagagta ataaa                                     35

<210> SEQ ID NO 38
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 38
tcattaaatt atgataatca tatttaccaa atgcc                                    35

<210> SEQ ID NO 39
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 39
agactacgta cataacctaa acctactcca atgct                                    35

```
<210> SEQ ID NO 40
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 40 aaaatttttgg tgcaactcca aataaaagta ataac                              35

<210> SEQ ID NO 41
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 41
ttggtcgtgg ttgtagtccg tgcgagaata atgat                               35

<210> SEQ ID NO 42
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 42
catcgttgta tttcaactac aagaacacca atgac                               35

<210> SEQ ID NO 43
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 43
wwaadwnktn nwnaaacycw amnhanmvwa atg                                 33

<210> SEQ ID NO 44
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 44
gaaaataaat tgttatcat ttt                                             23
```

```
<210> SEQ ID NO 45
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 45
tacagaaaat aaatttgtta tcattt                                              26

<210> SEQ ID NO 46
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 46

Met Met Thr Asn Leu Phe Ser Val
1               5

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
ttaaatttwt awwttaatta                                                     20

<210> SEQ ID NO 48
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 48
ttaaattcaa taaattgaaa atgataacaa atttattttc tgta                          44

<210> SEQ ID NO 49
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 49
ttaaattcaa taaattgaaa atgataacaa atttattctc tgta                          44

<210> SEQ ID NO 50
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 50
ttaaatttat atattaatta atgatgacga acctgttcag cgtg                          44
```

MITOCHONDRIAL TARGETED RNA EXPRESSION SYSTEM AND USE THEREOF

CROSS REFERENCE TO RELATED APPLICATIONS

This application claims the benefit of U.S. Provisional Application No. 61/622,649, filed Apr. 11, 2012, and U.S. Provisional Application No. 61/717,741, filed Oct. 24, 2012, both of which are herein incorporated by reference in their entirety.

ACKNOWLEDGMENT OF GOVERNMENT SUPPORT

This invention was made with government support under grant numbers NS078758, AG025046 and AG027453, awarded by the National Institutes of Health. The government has certain rights in the invention.

FIELD

This disclosure concerns compositions and methods for targeting RNA molecules to mitochondria, such as for use in gene therapy.

BACKGROUND

Mitochondria are cellular organelles found in eukaryotic cells that play a central role in energy metabolism, apoptosis and aging. Mitochondria contain a distinct mitochondrial genome, and human mitochondria (as well as mitochondria of other animals) contain 2 to 10 copies of mitochondrial DNA (mtDNA), which encodes essential components of the oxidative phosphorylation machinery. Proteins encoded by mtDNA are synthesized directly in the mitochondrion. Mitochondrial DNA resembles prokaryotic DNA in that it is a circular, double stranded molecule comprising genes that do not possess introns. The mitochondrion is highly susceptible to mutagenesis, and numerous mtDNA mutations are known to cause disease.

In mammals, the mtDNA encodes 13 proteins of the electron transport chain, 22 transfer RNAs (tRNAs) and two ribosomal RNAs (rRNAs)—12S and 16S rRNAs (Bibb et al., *Cell* 26:167-180, 1981; Anderson et al., *Nature* 290:457-465, 1981). There are currently more than 140 known protein-coding mutations affecting endogenous mitochondrial genes, resulting in a myriad of diseases with no current viable therapy. In addition, all of the key components of the electron transport chain are encoded by mitochondria, and electron transport dysfunction has been associated with every major neurodegenerative disease, including Parkinson's disease, Alzheimer's disease, Huntington's disease and amyotrophic lateral sclerosis. Thus, the ability to modulate mitochondrial function using a gene therapy or an inhibitor mechanism capable of expressing or repressing endogenous mitochondrial genes is desirable.

SUMMARY

Disclosed herein is a mitochondrial-targeted RNA expression system (mtTRES) for delivery of RNA molecules to mitochondria.

Provided herein is a vector comprising (in the 5' to 3' direction) an RNA polymerase III (RNAPIII) promoter sequence; a non-coding mitochondrial leader sequence; (i) a mitochondrial translation initiation sequence and an open reading frame (ORF) encoding a protein, or (ii) a sequence encoding a non-coding RNA molecule capable of inhibiting translation of a mitochondrial mRNA molecule; and an RNAPIII termination sequence. In particular non-limiting examples, at least one codon of the ORF is modified such that the protein can be translated in mitochondria but not in the cytosol.

Further provided are isolated host cells comprising an mtTRES or translation inhibition (TLI) vector disclosed herein.

Also provided herein are recombinant RNA molecules produced by expression of the vectors disclosed herein. The recombinant RNA molecules include a non-coding mitochondrial leader sequence; and (i) a mitochondrial translation initiation sequence and an ORF, or (ii) a non-coding RNA.

Further provided by the present disclosure is a method of targeting a recombinant RNA molecule to mitochondria of a cell by contacting the cell with a vector disclosed herein, wherein expression of the vector in the cell produces the recombinant RNA molecule which is targeted to the mitochondria. In some examples, the method is an in vitro method. In other examples, the method is an in vivo method.

Also provided is a method of treating a disease caused by a mutation in a mitochondrial gene. In some embodiments, the method includes selecting a subject with a disease caused by the mutation in the mitochondrial gene and administering to the subject a therapeutically effective amount of one or more mtTRES vectors as disclosed herein.

Also provided is a vector comprising (in the 5' to 3' direction) an RNAPIII promoter sequence; a non-coding mitochondrial leader sequence; a mitochondrial translation initiation sequence; an open reading frame (ORF) encoding a reporter protein; and an RNAPIII termination sequence, wherein at least one codon of the ORF is modified such that the reporter protein is translated in mitochondria but not in the cytosol. The vectors can be used, for example, in assays to detect mitochondrial RNA import and translation.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E are schematic illustrations of mtTRES RNAPIII expression vectors and confocal microscopy images showing reporter (eGFP) expression in mitochondria. (FIG. 1A) A schematic illustration showing vector organization including the location of useful restriction enzyme sequences for cloning purposes. (FIG. 1B) A schematic illustration of an exemplary vector with a mitochondrial translational initiation sequence and an ORF. (FIG. 1C) Confocal microscopy images showing eGFP fluorescence that co-localizes with mitotracker in primary neurons of transgenic flies. Bottom panels show a vector that does not express eGFP. (FIG. 1D) mtTRES-NCL::GFP transgenic *Drosophila* animals demonstrate function in vivo. The top panel shows mtTRES control lacking the GFP ORF. The middle and bottom images are from fly brains of mtTRES-MRP::eGFP and mtTRES-RNP::eGFP transgenic animals, respectively. (FIG. 1E) Quantitation of fluorescent data in (D) demonstrating that fluorescence is well above the background fluorescence observed in control brains. *** is p<0.0001 (Student's t-test).

(FIG. 3A) A sequence alignment of the 41 nucleotides 5' to the start of the 13 mitochondrially expressed proteins (SEQ ID NOs: 16-28) and a consensus sequence (SEQ ID NO: 29). (FIG. 3B) PRALINE multiple sequence alignment analysis to determine sequence conservation and percent usage of each nucleotide at each spot within the promoter sequence.

(FIG. 4A) Western blot to detect expression of ATP6 in ATP6 mutant ([1]), sesB mutant ([1]) and wild-type (+) flies. Detection of Sod2 expression was used as a protein expression control. (FIG. 4B) Quantitation of ATP6 protein expression in wild-type (WT), ATP6[1]/sesB[1], ATP[1] and sesB [1] flies.

(FIG. 5A) Survivorship of wild-type and TLI-5s::ATP6[1] transgenic flies. The ATP6 TLI inhibits translation of wild-type ATP6, resulting in a significant reduction in longevity. (FIG. 5B) Locomotor function in wild-type and TLI-5s::ATP6[1] transgenic flies. The ATP6 TLI causes a progressive reduction in locomotor function in vivo akin to ATP6[1] phenotypes. *** is p<0.0001 (one-way ANOVA). (FIG. 5C) Western blot (top) to detect ATPα (control) and ATP6 protein expression in flies comprising three different ATP6 TLI vectors, each with a different non-coding leader (NCL) sequence (MRP, 5s or RNP). Quantitation of the Western blot (bottom) demonstrated that ATP6 expression was reduced 35-50% (normalized to ATPα) resulting from ATP6 TLI. All three constructs with their independent NCLs were functional. * is p<0.03 and ** is p<0.005 (unpaired t-test). (FIG. 5D) Percent survival of *Drosophila* harboring one of three independent NCLrATP6 (modified with silent changes to be resistant to the TLI) vectors and the RNP:TLI to ATP6. All experimental groups are improved from the control, p<0.0001 by Prism log-rank analysis.

(FIG. 6A) Survivorship of wild-type and TLI-5s::COXII transgenic *Drosophila*. COXII TLI reduces *Drosophila* longevity. (FIG. 6B) Locomotor function in wild-type and TLI-5s::COXII transgenic *Drosophila*. The COXII TLI causes a progressive loss in locomotor function in vivo. * is p<0.05 (one-way ANOVA). (FIG. 6C) Western blot (top) to detect ATPα (control) and COXII protein expression in flies comprising the 5s and MRP NCL:TLI strains. Quantitation of the Western blot (bottom) demonstrated that COXII expression was reduced approximately 10-15% (normalized to ATPα) resulting from COXII TLI expression in vivo.  is p=0.0012 and * is p=0.0008 (unpaired t-test).

SEQUENCE LISTING

Figure 1D:
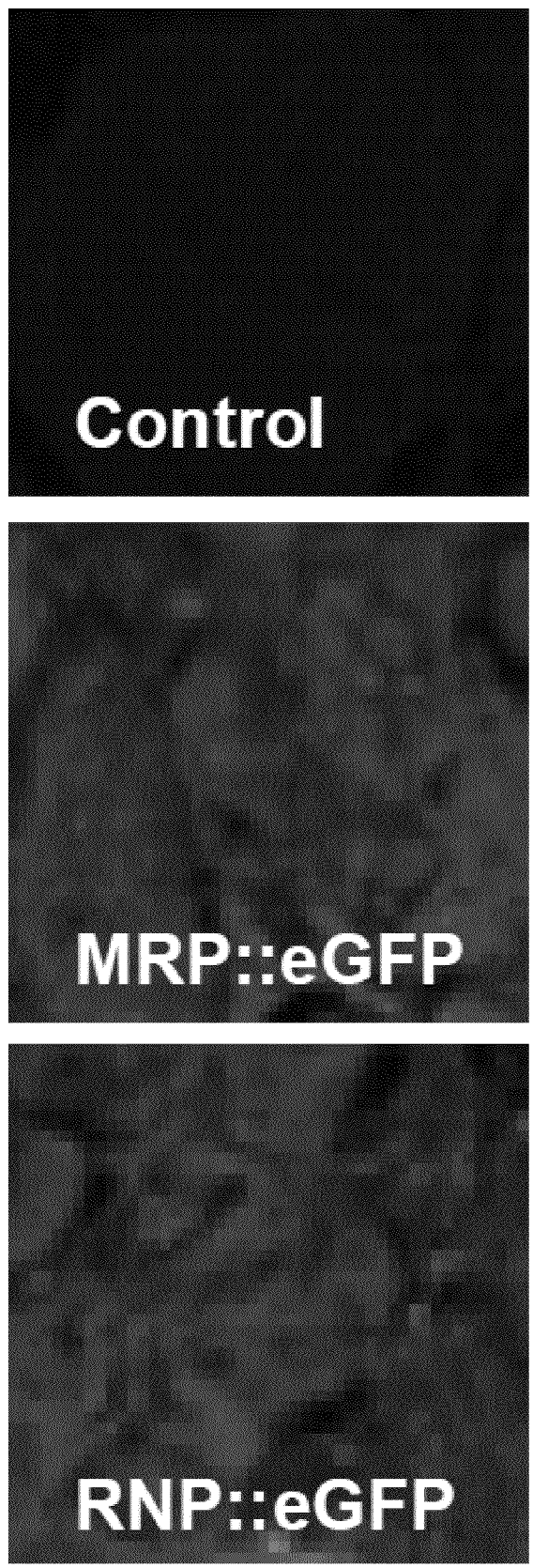

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 4, 2013, 14.5 KB, which is incorporated by reference herein. In the accompanying sequence listing:

SEQ ID NO: 1 is the RNA sequence of the 5S RNA non-coding leader (NCL).
SEQ ID NO: 2 is the DNA sequence of the 5S RNA NCL.
SEQ ID NO: 3 is the RNA sequence of the MRP NCL.
SEQ ID NO: 4 is the DNA sequence of the MRP NCL.
SEQ ID NO: 5 is the RNA sequence of the RNAseP NCL.
SEQ ID NO: 6 is the DNA sequence of the RNAseP NCL.
SEQ ID NO: 7 is the ATP6 translational initiation RNA sequence.
SEQ ID NO: 8 is the ATP6 translational initiation DNA sequence.
SEQ ID NO: 9 is the fly 5S RNAPIII promoter sequence.
SEQ ID NO: 10 is the human U6 RNAPIII promoter sequence.
SEQ ID NO: 11 is the fly 5S RNAPIII termination sequence.
SEQ ID NO: 12 is the ATP6 ORF RNA sequence.
SEQ ID NO: 13 is the ATP6 ORF DNA sequence.
SEQ ID NO: 14 is the eGFP ORF RNA sequence.
SEQ ID NO: 15 is the eGFP ORF DNA sequence.
SEQ ID NO: 16 is the nucleotide sequence of a portion of the fly ND2 promoter region.
SEQ ID NO: 17 is the nucleotide sequence of a portion of the fly COX1 promoter region.
SEQ ID NO: 18 is the nucleotide sequence of a portion of the fly COX2 promoter region.
SEQ ID NO: 19 is the nucleotide sequence of a portion of the fly ATP8 promoter region.
SEQ ID NO: 20 is the nucleotide sequence of a portion of the fly ATP6 promoter region.
SEQ ID NO: 21 is the nucleotide sequence of a portion of the fly COX3 promoter region.
SEQ ID NO: 22 is the nucleotide sequence of a portion of the fly ND3 promoter region.
SEQ ID NO: 23 is the nucleotide sequence of a portion of the fly ND5 promoter region.
SEQ ID NO: 24 is the nucleotide sequence of a portion of the fly ND4 promoter region.
SEQ ID NO: 25 is the nucleotide sequence of a portion of the fly ND4L promoter region.
SEQ ID NO: 26 is the nucleotide sequence of a portion of the fly ND6 promoter region.
SEQ ID NO: 27 is the nucleotide sequence of a portion of the fly CYTO-B promoter region.
SEQ ID NO: 28 is the nucleotide sequence of a portion of the fly ND1 promoter region.
SEQ ID NO: 29 is the nucleotide consensus sequence of a portion of the promoter region from 13 fly mitochondrial genes.
SEQ ID NO: 30 is the nucleotide sequence of a portion of the human ND1 promoter region.
SEQ ID NO: 31 is the nucleotide sequence of a portion of the human ND2 promoter region.
SEQ ID NO: 32 is the nucleotide sequence of a portion of the human COX1 promoter region.
SEQ ID NO: 33 is the nucleotide sequence of a portion of the human COX2 promoter region.
SEQ ID NO: 34 is the nucleotide sequence of a portion of the human ATP8 promoter region.
SEQ ID NO: 35 is the nucleotide sequence of a portion of the human ATP6 promoter region.
SEQ ID NO: 36 is the nucleotide sequence of a portion of the human COX3 promoter region.
SEQ ID NO: 37 is the nucleotide sequence of a portion of the human ND3 promoter region.
SEQ ID NO: 38 is the nucleotide sequence of a portion of the human ND4L promoter region.

SEQ ID NO: 39 is the nucleotide sequence of a portion of the human ND4 promoter region.

SEQ ID NO: 40 is the nucleotide sequence of a portion of the human ND5 promoter region.

SEQ ID NO: 41 is the nucleotide sequence of a portion of the human ND6 promoter region.

SEQ ID NO: 42 is the nucleotide sequence of a portion of the human CYTB promoter region.

SEQ ID NO: 43 is the nucleotide consensus sequence of a portion of the promoter region from 13 human mitochondrial genes.

SEQ ID NO: 44 is the nucleotide sequence of ATP6-TLI #1.

SEQ ID NO: 45 is the nucleotide sequence of ATP6-TLI #2.

SEQ ID NO: 46 is the amino acid sequence of a portion of the ATP6 protein.

SEQ ID NO: 47 is a nucleotide consensus sequence of the promoter region immediately 5' of the coding sequence of the 13 mitochondrial genes.

SEQ ID NO: 48 is the nucleotide sequence of a portion of the endogenous ATP6 locus.

SEQ ID NO: 49 is the nucleotide sequence of a portion of the mtTRES-ATP6 construct.

SEQ ID NO: 50 is the nucleotide sequence of a portion of the mtTRES-rATP6 construct.

DETAILED DESCRIPTION

I. Abbreviations

ATP6 ATP synthase F0 subunit 6
eGFP enhanced green fluorescent protein
MRP mitochondrial ribosomal protein
mtDNA mitochondrial DNA
mtTRES mitochondrial-targeted RNA expression system
NCL non-coding leader
ORF open reading frame
RFLP restriction fragment length polymorphism
RNAPIII RNA polymerase III
rRNA ribosomal RNA
snRNA small nuclear RNA
TLI translational inhibition
tRNA transfer RNA

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

5S rRNA: A component of the large ribosomal subunit in both prokaryotes (50S) and eukaryotes (60S). Eukaryotic 5S rRNA is synthesized by RNA polymerase III.

Administration: To provide or give a subject an agent, such as a therapeutic agent (e.g. a nucleic acid molecule or vector), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Alzheimer's disease (AD): A progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years. AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning.

Amyotrophic lateral sclerosis (ALS): A progressive, usually fatal, neurodegenerative disease caused by the degeneration of motor neurons. As a motor neuron disease, the disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. The patient may ultimately lose the ability to initiate and control all voluntary movement except for the eyes. ALS is also known as Lou Gehrig's disease.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to administration of a compound (such as a vector) to a subject.

Disease caused by a mutation in a mitochondrial gene: Refers to any disease or disorder resulting at least in part due to a mutation in a gene encoded by mitochondrial DNA. In some embodiments, the mutation is in a gene encoding a protein of the electron transport chain. In some embodiments, the disease is associated with electron transport chain or ATP synthase dysfunction. In some examples, the disease is a neurodegenerative disease, such as Alzheimer's disease, Parkinson's disease, ALS or Huntington's disease. In other examples, the disease is a cardiac disease; autism; diabetes mellitus (or diabetes mellitus and deafness); a mitochondrial myopathy; Leber's hereditary optic neuropathy; Leigh syndrome; neuropathy, ataxia, retinitis pigmentosa, and ptosis (NARP); myoneurogenic gastrointestinal encephalopathy (MNGIE); myoclonic epilepsy with ragged red fibers (MERRF); mitochondrial myopathy, encephalomyopathy, lactic acidosis, stroke-like symptoms (MELAS); mitochondrial neurogastrointestinal encephalomyopathy (MNGIE); Kearns-Sayre syndrome; or any other disease affected by mitochondrial function.

Electron transport chain: A spatially separated series of redox reactions in which electrons are transferred from a donor molecule to an acceptor molecule. Most eukaryotic cells have mitochondria, which produce ATP from products of the citric acid cycle, fatty acid oxidation, and amino acid oxidation. At the mitochondrial inner membrane, electrons from NADH and succinate pass through the electron transport chain to oxygen, which is reduced to water. The electron transport chain comprises an enzymatic series of electron donors and acceptors. Each electron donor passes electrons to a more electronegative acceptor, which in turn donates these electrons to another acceptor, a process that continues down the series until electrons are passed to oxygen, the most electronegative and terminal electron acceptor in the chain. Passage of electrons between donor and acceptor releases energy, which is used to generate a proton gradient across the mitochondrial membrane by actively "pumping" protons into the intermembrane space, producing a thermodynamic state that has the potential to do work. The entire process is called oxidative phosphorylation, since ADP is phosphorylated to ATP using the energy of hydrogen oxidation in many steps. Four major protein-membrane complexes of the electron transport chain have been identified in mitochondria—Complex I (NADH dehydrogenase), Complex II (succinate dehydrogenase), Complex III (cytochrome $bc_1$ complex) and Complex IV (cytochrome c oxidase). The ATP synthase is known as Complex V.

Huntington's disease (HD): A neurodegenerative genetic disorder that affects muscle coordination and leads to cognitive decline and psychiatric problems. The disease is caused by an autosomal dominant mutation in the Huntingtin gene. Expansion of a CAG triplet stretch within the Huntingtin gene results in a mutant form of the huntingtin protein, which gradually damages cells in the brain. Physical symptoms of the disease can begin at any age, but typically arise between ages 35 and 44. The earliest symptoms are often subtle problems with mood or cognition. A general lack of coordination and an unsteady gait often follows. As the disease progresses, uncoordinated, jerky body movements become more apparent, along with a decline in mental abilities and behavioral and psychiatric problems. Physical abilities are gradually impeded until coordinated movement becomes very difficult. Mental abilities generally decline into dementia.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Mitochondrial gene: A gene encoded by mitochondrial DNA. In mammals, the mitochondrial genome includes 13 protein-coding genes, two ribosomal RNA (rRNA) genes (encoding 12S and 16S rRNA) and 22 transfer RNA (tRNA) genes. The protein-coding genes encode proteins of the electron transport chain:

| Category | Genes |
|---|---|
| Complex I (NADH dehydrogenase) | ND1, ND2, ND3, ND4, ND4L, ND5, ND6 |
| Complex III (cytochrome $bc_1$ complex) | CYTB |
| Complex IV (cytochrome c oxidase) | COX1, COX2, COX3 |
| ATP synthase | ATP6, ATP8 |

Mitochondrial leader sequence: A non-coding nucleic acid sequence that is capable of directing import of an RNA into mitochondria. The mitochondrial leader sequence is also referred to herein as a "non-coding leader" or "NCL" sequence. In some embodiments, the mitochondrial leader sequence is a sequence from a 5S rRNA, such as the fly 5S rRNA variant V. In other embodiments, the NCL is from the RNA component of the endoribonuclease known as MRP (referred to herein as the MRP leader sequence), or the RNA component of the ribonucleoprotein known as RNAse P (referred to herein as the RNAse P leader sequence). In particular examples, the NCL comprises the nucleotide sequence of SEQ ID NO: 2, SEQ ID NO: 4 or SEQ ID NO: 6. Example 1 below describes a method for identifying suitable NCL sequences for use with the disclosed vectors.

Mitochondrial translation initiation sequence: A nucleic acid sequence that mediates the initiation of translation of an RNA in mitochondria. A translation initiation sequence is typically found upstream (5') of a translational start codon. Example 1 describes one method for the identification of a suitable translation initiation sequence for use with the disclosed vectors. In some embodiments, the translation initiation sequence is represented by the consensus sequence of nucleotides 19-38 of SEQ ID NO: 29 or nucleotides 11-30 of SEQ ID NO: 43. In particular examples, the translation initiation sequence comprises nucleotides 19-38 of any one of SEQ ID NOs: 16-28 or nucleotides 11-30 of any one of SEQ ID NOs: 30-42.

Neurodegenerative disease: Refers to any type of disorder or disease that is associated with a progressive loss of motor, sensory and/or perceptual functions, and often involves behavioral and cognitive deficits. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

Non-coding RNA: Any RNA molecule that does not encode a protein. In the context of the present disclosure, a non-coding RNA molecule encoded by the mtTRES vectors disclosed herein is an RNA that inhibits translation of a mitochondrial mRNA. In some embodiments, the non-coding RNA specifically hybridizes with a translation initiation site of a mitochondrial mRNA.

ORF (open reading frame): A series of nucleotide triplets (codons) coding for amino acids without any termination codons. These sequences are usually translatable into a peptide.

Parkinson's disease (PD): A degenerative disorder of the central nervous system that impairs motor skills, cognitive processes, and other functions. Parkinson's disease is also referred to as Parkinson disease, Parkinson's, PD and primary Parkinsonism. The most obvious symptoms of Parkinson's disease are motor-related, including tremor, rigidity, slowness of movement and postural instability. Among non-motor symptoms are autonomic dysfunction and sensory and sleep difficulties. Cognitive and neurobehavioral problems, including dementia, are common in the advanced stages of the disease.

In subjects that develop Parkinson's disease, symptoms typically begin around the age of 60, although there are young-onset cases. Symptoms result from insufficient formation and action of dopamine produced in the dopaminergic neurons of the midbrain (specifically the substantia nigra). Pathologically the disease is characterized by the accumulation of alpha-synuclein protein forming inclusions called Lewy bodies. Such pathology can only be demonstrated at autopsy so diagnosis is mainly clinical (based on symptoms). Some tests such as neuroimaging techniques can also aid in diagnosis.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences that directs transcription of a nucleic acid. A promoter includes necessary nucleic acid sequences near the start site of transcription. A promoter also optionally includes distal enhancer or repressor elements which can be located as much as several thousand base pairs from the start site of transcription. Both constitutive and inducible promoters are included (see e.g., Bitter et al., *Methods in Enzymology* 153: 516-544, 1987).

Recombinant: A recombinant nucleic acid molecule or peptide is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

RNA polymerase III (RNAPIII): An enzyme that transcribes DNA to synthesize ribosomal 5S rRNA, tRNA and other small RNAs. As used herein, an "RNAPIII promoter sequence" is a promoter sequence recognized by RNAPIII to initiation transcription. In some embodiments, the RNAPIII promoter sequence is a 5S rRNA or U6 RNAPIII promoter sequence. In particular examples, the RNAPIII promoter sequence is at least 95% identical to SEQ ID NO: 9 or SEQ ID NO: 10. Similarly, an "RNAPIII termination sequence" is a nucleic acid sequence that RNAPIII recognizes as a transcription termination sequence. In some embodiments, the RNAPIII termination sequence is a 5S rRNA RNAPIII termination sequence. In particular examples, the RNAPIII termination sequence is at least 95% identical to SEQ ID NO: 11. Although exemplary RNAPIII promoter and termination sequences are provided herein, one of skill in the art will understand that a variety of RNAPIII promoter and termination sequences are known and could function in the context of the vectors described herein. For example, Schramm and Hernandez (*Genes Dev* 16:2593-2620, 2002) describe RNAPIII promoter structure and sequence variations, and Orioli et al. (*Nucleic Acids Res* 39(13):5499-5512, 2011) and Gunnery et al. (*J Mol Biol* 286(3):745-757, 1999) teach variations in RNAPIII termination signal sequences.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

In some embodiments, provided herein are nucleic acid molecules at least 80%, at least 85%, at least 90%, at least 95%, at least 96%, at least 97%, at least 98% or at least 99% identical to any one of SEQ ID NOs: 1-43.

Subject: Living multi-cellular vertebrate organisms, a category that includes both human and veterinary subjects, including human and non-human mammals (including research subjects such as rodents). A subject is also referred to herein as a "patient."

Therapeutically effective amount: A quantity of a specified composition, pharmaceutical or therapeutic agent (such as a nucleic acid molecule or vector) sufficient to achieve a desired effect in a subject, or in a cell, being treated with the agent. The effective amount of the agent will be dependent on several factors, including, but not limited to the subject being treated, the disease or condition being treated, and the manner of administration of the therapeutic composition. In some embodiments of the present disclosure, the therapeutically effective amount (or effective amount) of a mitochondrial-targeted RNA expression system vector is an amount sufficient to ameliorate one or more signs or symptoms of a disease caused by a mutation in a mitochondrial gene (such as a disease associated with electronic transport chain or ATP synthase dysfunction, for example a neurodegenerative disease), delay the progression of the disease, and/or prolong survival of the subject with the disease.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the development of a mitochondrial-targeted RNA expression system (mtTRES) for delivery of RNA molecules to mitochondria. In particular, disclosed are mtTRES vectors that generate RNAs in vivo that are un-capped, non-polyadenylated, and actively directed to mitochondria. The disclosed vectors are capable of delivering to mitochondria non-coding RNA molecules (such as for inhibiting translation of a mitochondrial mRNA) or RNA molecules encoding a protein of interest (such as for gene therapy applications). In some embodiments, both types are vectors are used together to specifically inhibit translation of a mutant protein and simultaneously provide wild-type protein.

In some embodiments, the vector comprises in the 5' to 3' direction, an RNA polymerase III (RNAPIII) promoter sequence; a non-coding mitochondrial leader sequence; a mitochondrial translation initiation sequence and an open reading frame (ORF) encoding a protein, or a sequence encoding a non-coding RNA molecule capable of inhibiting translation of a mitochondrial mRNA molecule; and an RNAPIII termination sequence.

The RNAPIII promoter sequence can be any nucleic acid sequence that is recognized by RNAPIII to initiate transcription. In some embodiments, the RNAPIII promoter sequence is a 5S rRNA RNAPIII promoter sequence or a U6 RNAPIII promoter sequence. In particular examples, the RNAPIII promoter sequence is at least 80%, at least 85%, at least 90%, at least 95%, at least 96%, at least 97%, at least 98% or at least 99% identical to SEQ ID NO: 9 or SEQ ID NO: 10. In specific non-limiting examples, the RNAPIII promoter sequence comprises or consists of SEQ ID NO: 9 or SEQ ID NO: 10.

The RNAPIII termination sequence can be any nucleic acid sequence that RNAPIII recognizes as a transcription termination sequence. In some embodiments, the RNAPIII termination sequence is a 5S rRNA RNPAIII termination sequence. In particular examples, the 5S rRNA RNPAIII termination sequence is at least 80%, at least 85%, at least 90%, at least 95%, at least 96%, at least 97%, at least 98% or at least 99% identical to SEQ ID NO: 11. In specific non-limiting examples, the RNAPIII termination sequence comprises or consists of SEQ ID NO: 11.

The non-coding mitochondrial leader sequence can be any nucleic acid sequence that is capable of directing import of an RNA into mitochondria. In some embodiments, the mitochondrial leader sequence comprises a 5S rRNA leader sequence (such as from the fly 5S rRNA variant V), an MRP leader sequence (from the RNA component of the MRP endoribonuclease) or an RNAseP leader sequence (from the RNA component of the RNAse P ribonucleoprotein). In particular examples, the 5S rRNA leader sequence is at least 80%, at least 85%, at least 90%, at least 95%, at least 96%, at least 97%, at least 98% or at least 99% identical to SEQ ID NO: 2; the MRP leader sequence is at least 80%, at least 85%, at least 90%, at least 95%, at least 96%, at least 97%, at least 98% or at least 99% identical to SEQ ID NO: 4; or the RNAseP leader sequence is at least 80%, at least 85%, at least 90%, at least 95%, at least 96%, at least 97%, at least 98% or at least 99% identical to SEQ ID NO: 6. In specific non-limiting examples, the non-coding mitochondrial leader sequence comprises or consists of SEQ ID NO: 2, SEQ ID NO: 4 or SEQ ID NO: 6.

In some embodiments of the disclosed vectors, at least one codon of the ORF is modified such that the protein can be translated in mitochondria but not in the cytosol. For example, the codon can be modified to introduce a premature stop codon to prevent expression of the protein (or expression of the full-length protein) in the cytosol. This effect can be achieved by taking advantage of codon differences between the cytosol and mitochondria.

The mitochondrial translation initiation sequence can be any nucleic acid sequence that mediates the initiation of translation of an RNA in mitochondria. For example, suitable translation initiation sequences can be found upstream (5') of a translational start codon of a mitochondrial gene. In some embodiments, the mitochondrial translation initiation sequence is at least 80%, at least 85%, at least 90%, at least 95%, at least 96%, at least 97%, at least 98% or at least 99% identical to nucleotides 19-38 of SEQ ID NO: 29 or nucleotides 11-30 of SEQ ID NO: 43. In some embodiments, the mitochondrial translation initiation sequence comprises or consists of nucleotides 19-38 of SEQ ID NO: 29 or nucleotides 11-30 of SEQ ID NO: 43. In some examples, the mitochondrial translation initiation sequence comprises or consists of SEQ ID NO: 29 or SEQ ID NO: 43. In particular examples, the mitochondrial translation initiation sequence is at least 80%, at least 85%, at least 90%, at least 95%, at least 96%, at least 97%, at least 98% or at least 99% identical to nucleotides 19-38 of any one of SEQ ID NOs: 16-28 or nucleotides 11-30 of any one of SEQ ID NOs: 30-42. In other particular examples, the mitochondrial translation initiation sequence comprises or consists of nucleotides 19-38 of any one of SEQ ID NOs: 16-28 or nucleotides 11-30 of any one of SEQ ID NOs: 30-42. In other particular examples, the mitochondrial translation initiation sequence comprises or consists of any one of SEQ ID NOs: 16-28 or SEQ ID NOs: 30-42. In one non-limiting example, the mitochondrial translation initiation sequence comprises or consists of SEQ ID NO: 8.

The disclosed vectors can include an ORF encoding any protein of interest. In some embodiments, the ORF encodes a protein encoded by a mitochondrial gene. In some examples, the protein is encoded by the ND1, ND2, ND3, ND4, ND4L, ND5, ND6, CYTB, COX1, COX2, COX3, ATP6 or ATP8 gene. In other embodiments, the ORF encodes a reporter protein, such as a fluorescent protein.

The disclosed vectors can encode any non-coding RNA that inhibits translation of a mitochondrial mRNA. In some embodiments, the non-coding RNA specifically hybridizes with a translation initiation site of the mRNA molecule, thereby inhibiting translation.

In some embodiments, the vector is a viral vector. Suitable viral vectors for administration to a cell or a subject are well known in the art. In particular examples, the viral vector is an adenovirus, adeno-associated virus, retrovirus, herpes virus or vaccinia virus vector. Viral vectors can include modified versions of the viruses, such as replication deficient viruses. In other embodiments, the vector is a plasmid vector.

Further provided herein are isolated host cells comprising a vector as disclosed herein.

Also provided are recombinant RNA molecules produced by expression of a vector as disclosed herein, wherein the recombinant RNA molecule comprises a non-coding mitochondrial leader sequence; and (i) a mitochondrial translation initiation sequence and an ORF, or (ii) a non-coding RNA.

In some embodiments of the recombinant RNA molecule, the non-coding mitochondrial leader sequence comprises a 5S rRNA leader sequence, an MRP leader sequence or an RNAseP leader sequence. In some examples, the 5S rRNA leader sequence is at least 80%, at least 85%, at least 90%, at least 95%, at least 96%, at least 97%, at least 98% or at least 99% identical to SEQ ID NO: 1; the MRP leader sequence is at least 80%, at least 85%, at least 90%, at least 95%, at least 96%, at least 97%, at least 98% or at least 99% identical to SEQ ID NO: 3; or the RNAseP leader sequence is at least 80%, at least 85%, at least 90%, at least 95%, at least 96%, at least 97%, at least 98% or at least 99% identical to SEQ ID NO: 5. In particular non-limiting examples, the non-coding mitochondrial leader sequence comprises or consists of SEQ ID NO: 1, SEQ ID NO: 3 or SEQ ID NO: 5.

In some embodiments of the recombinant RNA molecules, the mitochondrial translation initiation sequence is at least 80%, at least 85%, at least 90%, at least 95%, at least 96%, at least 97%, at least 98% or at least 99% identical to SEQ ID NO: 7. In particular examples, the mitochondrial translation initiation sequence comprises or consists of SEQ ID NO: 7.

Further provided herein is a method of targeting a recombinant RNA molecule to mitochondria of a cell, comprising contacting the cell with a vector as disclosed herein, wherein expression of the vector in the cell produces the recombinant RNA molecule which is targeted to mitochondria. In some embodiments, the method is an in vitro method. In other embodiments, the method is an in vivo method.

Also provided herein is a method of treating a disease caused by a mutation in a mitochondrial gene. In some embodiments, the method includes selecting a subject with a disease caused by the mutation in the mitochondrial gene and administering to the subject a therapeutically effective amount of a vector disclosed herein.

In some embodiments of the treatment method, the disease is associated with electron transport chain or ATP synthase dysfunction.

In some embodiments of the treatment method, the disease is a neurodegenerative disease. In particular examples, the neurodegenerative disease comprises Parkinson's disease, Alzheimer's disease, Huntington's disease or amyotrophic lateral sclerosis.

The present disclosure also encompasses the use of more than one mtTRES vector in combination for the treatment of disease. For example, a subject can be administered a first vector expressing a coding RNA for wild-type protein (the rescue vector) and a second vector expressing a non-coding RNA that inhibits translation of the corresponding mutant protein (the translational inhibition vector). The combination of the two vectors simultaneously inhibits translation of the mutant protein and provides wild-type protein to rescue the defect caused by the mutant mitochondrial gene.

Thus, in some embodiments, the subject is administered a first vector and a second vector, wherein the first vector comprises a mitochondrial translation initiation sequence and an ORF encoding a protein (a rescue vector), and the second vector comprises a sequence encoding a non-coding RNA molecule capable of inhibiting translation of a mitochondrial mRNA molecule (a TLI vector). In some examples, the disease is caused by a mutation in the ATP6 gene, and the ORF of the first vector encodes a wild-type ATP6 protein and the non-coding RNA molecule of the second vector inhibits translation of mutant ATP6 mRNA. In some examples, the first vector comprises one or more silent mutations in the ORF such that translation of the protein is not inhibited by the non-coding RNA molecule of the second vector. In other embodiments, the disease is caused by a mutation in the COX2 gene.

Further provided is a vector comprising in the 5' to 3' direction an RNAPIII promoter sequence; a non-coding mitochondrial leader sequence; a mitochondrial translation initiation sequence; an open reading frame (ORF) encoding a reporter protein; and an RNAPIII termination sequence, wherein at least one codon of the ORF is modified such that the reporter protein is translated in mitochondria but not in the cytosol. In some embodiments, the reporter protein is a fluorescent protein. In specific examples, the fluorescent protein is a GFP, such as enhanced GFP (eGFP) or any modified variant fluorescent protein.

In some embodiments of the vectors disclosed herein, the codon of the ORF is modified to contain a premature stop codon if translated in the cytosol and a tryptophan codon is translated in mitochondria.

The following examples are provided to illustrate certain particular features and/or embodiments. These examples should not be construed to limit the disclosure to the particular features or embodiments described.

EXAMPLES

Example 1

Mitochondrial-Targeted RNA Expression System (mtTRES)

This example describes the development of mitochondrial-targeted RNA expression system (mtTRES) vectors for delivery of RNA molecules to mitochondria, such as for use in gene therapy.

mtTRES vectors were developed to generate RNAs in vivo that are un-capped, non-polyadenylated, and actively directed to mitochondria. mtTRES vectors contain RNAPIII initiation (promoter) sequences, a non-coding leader sequence (NCL) and an RNAPIII termination sequence. Such a system can be used to generate non-coding RNAs, such as RNAs capable of mitochondrial translational inhibition by complementing sequences (such as the start codon of mitochondrial genes) and competing with the ribosome for access to the open reading frame (ORF). This results in a decrease in the level of protein of interest. Such a system is also capable of generating protein coding RNAs by the inclusion of a mitochondrial translation initiation sequence 5' to an ORF, for the purpose of introducing a wild-type version of a mutated protein or introduction of a protein not normally found in mitochondria.

Figure 1E:
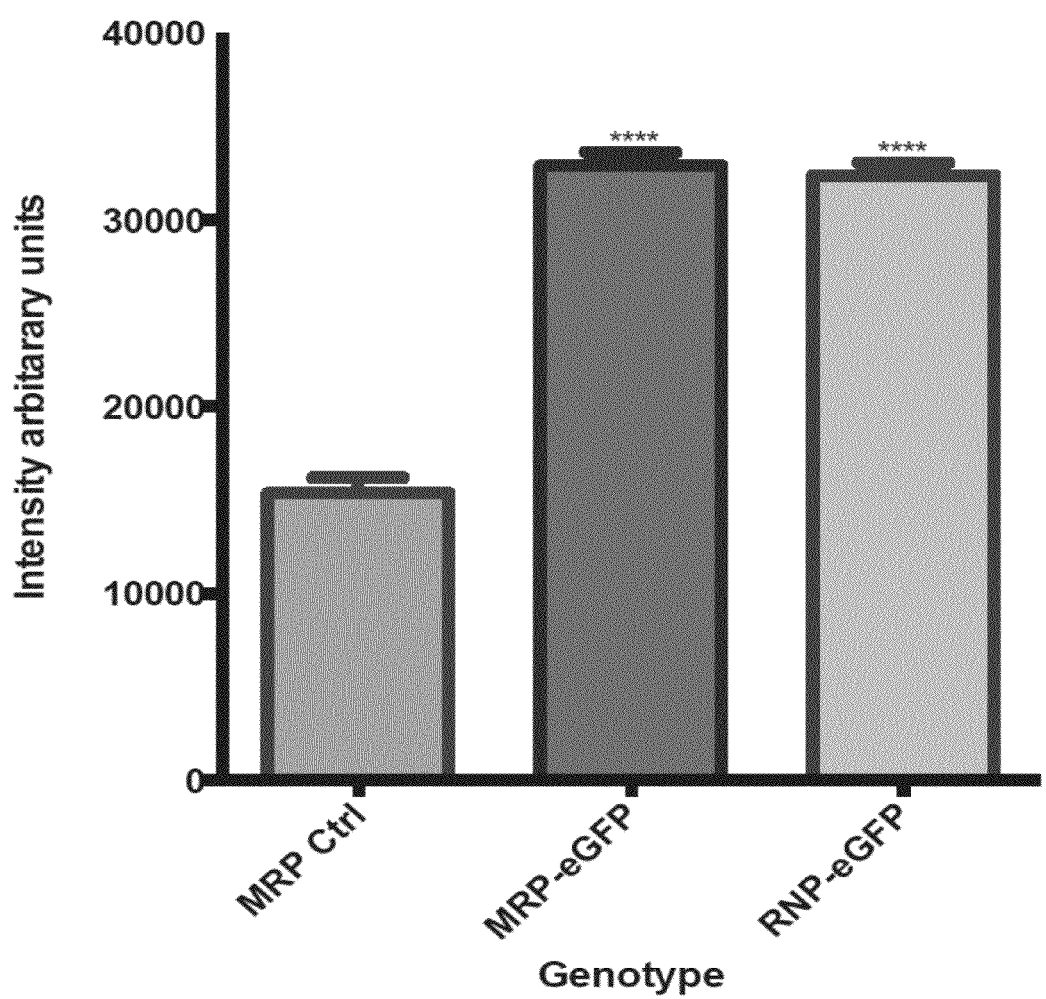
Figure 2:
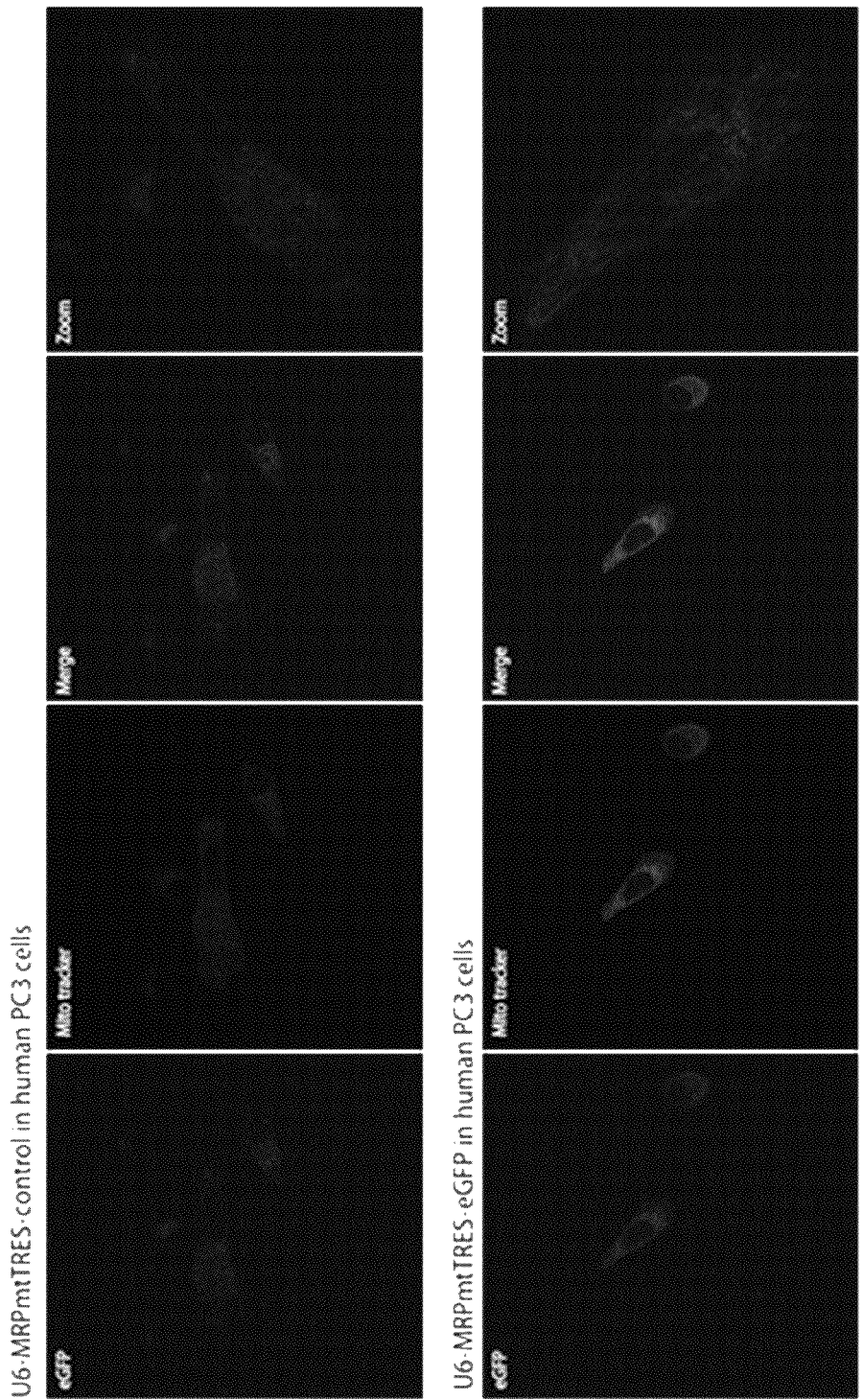
FIG. 2 is a series of confocal microscopy images demonstrating that human PC3 cells import eGFP coding RNAs. Top panels show control cells lacking the ORF. Bottom panels show cells that have the eGFP ORF and express fluorescence that co-localizes with mitotracker (merge) and clearly exhibit a reticular network similar to that of healthy mitochondria (zoom).

Described below is the generation of three specific vectors, mtTRES-5S::eGFP, mtTRES-MRP::eGFP, and mtTRES-RNAseP::eGFP, where 5S, MRP and RNAseP represent different NCLs. These vectors use RNAPIII promoter sequence from the 5S rRNA gene in flies and RNAPIII termination sequences. Mammalian versions of these vectors have also been generated that use the human U6 RNAPIII promoter. The data disclosed herein show that the mtTRES vectors are capable of directing nuclear expressed RNAs bearing ORFs to the mitochondria for translation in neurons from transgenic flies (FIG. 1) and in human PC3 cells (FIG. 2).

Cloning of the Backbone

The pUAST-attB vector is a publically available vector (Bischof et al., *Proc Natl Acad Sci USA* 104:3312-3317, 2007). All but the transformation backbone of this vector (containing the attB, bacterial origin of replication, AMP resistance and white$^{mc+}$ functional elements) was replaced. The HindIII-EcoRI fragment was replaced with the RNAPIII promoter sequence. A StuI site was introduced 5' to the attP site using site-directed mutagenesis (Quick change lightning, Invitrogen) and the KpnI-StuI fragment was replaced with the RNAPIII termination sequence. NCLs were introduced as EcoRI-EagI fragments and ORFs were cloned using EagI-KpnI. All cloning was directional using standard techniques and each step was verified initially by RFLP analyses and sequence confirmed (FIG. 1A).

Non-Coding Leaders (NCLs)

It has previously been described that the 5S rRNA genes are expressed in arrays within the nucleus yet the rRNAs can readily be found in mitochondria (Artavanis-Tsakonas et al., *Cell* 12:1057-1067, 1977; Benhamou and Jordan, *FEBS Lett* 62:146-149, 1976). Using the completed sequenced genome, 100 distinct 5S rRNA genes were identified and then organized into 17 genomic variants and 15 distinct processed rRNAs. A clonal analysis was performed to identify the sequence of the 5S rRNAs that are actively imported into mitochondria. Variant V is the most abundant mitochondrial localized 5S rRNA accounting for 88% of these RNAs, demonstrating its competence for import and suggesting this small RNA could function well as an NCL. Additionally, a recent study identified RNA elements that are encoded by the MRP and RNase P genes, which are recognized by PNPase (polynucleotide phosphorylase) and are themselves capable of mitochondrial import in vitro using synthesized RNAs (Wang et al., *Cell* 142:456-467, 2010).

The NCLs used in developing the mtTRES included the fly 5S rRNA variant V, and the MRP and RNase P RNA elements. The 5S NCL was synthesized and the MRP and RNAseP DNAs were made as oligos that were annealed. In all cases the NCLs were cloned into the mtTRES vector using EcoRI-EagI cloning sites and standard directional cloning techniques. It is expected that other sequences capable of this function can be identified using similar methods, such as clonal analysis of mitochondrial 5S rRNAs from other species. The sequences of the NCLs are shown below.

```
5SRNA NCL RNA sequence(SEQ ID NO: 1):
GCCAACGACCAUACCACGCUGAAUACAUCGGUUCUCGUCCGAUCACCG
AAAUUAAGCAGCGUCGGGCGCGGUUAGUACUUAGAUGGGGGACCGCUU
GGGAACACCGCGUGUUGUUGGCCU 5SRNA NCL DNA sequence(SEQ ID NO: 2):
GCCAACGACCATACCACGCTGAATACATCGGTTCTCGTCCGATCACCG
AAATTAAGCAGCGTCGGGCGCGGTTAGTACTTAGATGGGGGACCGCTT
GGGAACACCGCGTGTTGTTGGCCT
```

-continued

MRP NCL RNA sequence (SEQ ID NO: 3):
AGAAGCGUAUCCCGCUGAGC

MRP NCL DNA sequence (SEQ ID NO: 4):
AGAAGCGTATCCCGCTGAGC

RNAseP NCL RNA sequence (SEQ ID NO: 5):
UCUCCCUGAGCUUCAGGGAG

RNAseP NCL DNA sequence (SEQ ID NO: 6):
TCTCCCTGAGCTTCAGGGAG

Translational Initiation

Figures 3A, 3B:
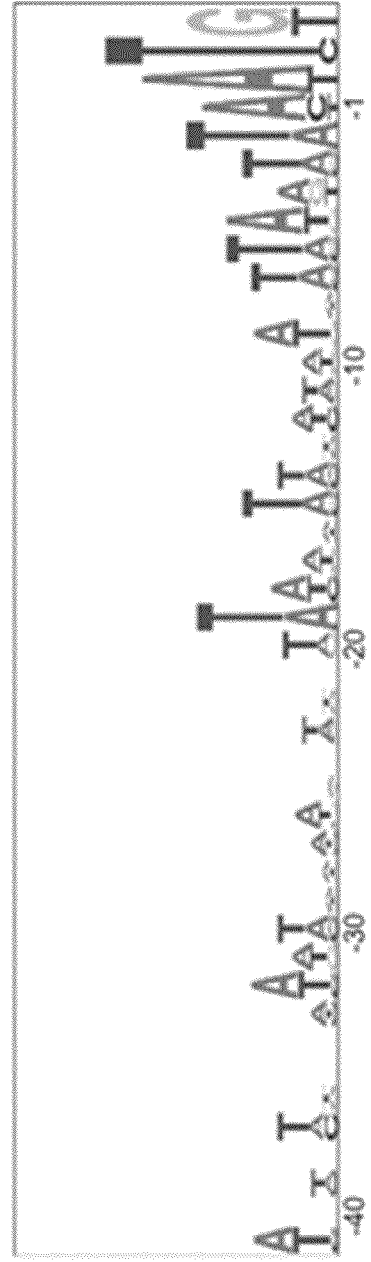
FIGS. 3A-3B show the promoter sequence of the 13 proteins expressed in the mitochondria of the fly (*Drosophila melanogaster*).

To engineer an RNAPIII generated RNA capable of expression within the mitochondrion, the sequences upstream of the translational start codon were examined for the 13 protein coding genes in the *Drosophila* mitochondrial genome. The sequence analysis suggested that the required sequences are within the 20 nucleotides 5' to the start codons and that any of these sequences or the consensus sequence would be sufficient (see FIG. 3 and SEQ ID NOs: 16-29). A similar analysis was then performed for the same 13 protein coding genes in humans and a highly similar 20 nucleotide consensus sequences was generated. Shown below are the promoter sequences of positions −30 to +5 relative to the start codon (underlined) for each human gene.

|  | (SEQ ID NO: 30) |
|---|---|
| ND1 | GTCAGAGGTTCAATTCCTCTTCTTAACAACATACC |
|  | (SEQ ID NO: 31) |
| ND2 | GAAAATGTTGGTTATACCCTTCCCGTACTAATTAA |
|  | (SEQ ID NO: 32) |
| COX1 | TCACTCAGCCATTTTACCTCACCCCCACTGATGTT |
|  | (SEQ ID NO: 33) |
| COX2 | TAAATTATAGGCTAAATCCTATATATCTTAATGGC |
|  | (SEQ ID NO: 34) |
| ATP8 | TTAAGAGAACCAACACCTCTTTACAGTGAAATGCC |
|  | (SEQ ID NO: 35) |
| ATP6 | AAAAAATTATAACAAACCCTGAGAACCAAAATGAA |
|  | (SEQ ID NO: 36) |
| COX3 | AGTAAGCCTCTACCTGCACGACAACACATAATGAC |
|  | (SEQ ID NO: 37) |
| ND3 | ACTAGTTTTGACAACATTCAAAAAAGAGTAATAAA |
|  | (SEQ ID NO: 38) |
| ND4L | TCATTAAATTATGATAATCATATTTACCAAATGCC |
|  | (SEQ ID NO: 39) |
| ND4 | AGACTACGTACATAACCTAAACCTACTCCAATGCT |
|  | (SEQ ID NO: 40) |
| ND5 | AAAATTTTGGTGCAACTCCAAATAAAAGTAATAAC |
|  | (SEQ ID NO: 41) |
| ND6 | TTGGTCGTGGTTGTAGTCCGTGCGAGAATAATGAT |
|  | (SEQ ID NO: 42) |
| CYTB | CATCGTTGTATTTCAACTACAAGAACACCAATGAC |

Human consensus sequence:

(SEQ ID NO: 43)
WWAADWNKTNNWNAAACYCWAMNHANMVWAATG

The 20 nucleotide sequence 5' to the start codon of fly ATP6 was tested for its translational initiation ability and was found to be functional. The ATP6 translational RNA and DNA sequences are shown below.

ATP6 Translational initiation RNA sequence
(SEQ ID NO: 7):
UUAAAUUCAAUAAAUUGAAA

ATP6 Translational initiation DNA sequence
(SEQ ID NO: 8)
TTAAATTCAATAAATTGAAA

RNAP III Promoter and Termination Sites

A vector containing an RNA polymerase III (RNAPIII) promoter and termination sequences that direct expression of stable RNAs from the nucleus in vivo has been developed. The 5SrRNA promoter and terminator sequences were used, similar to those previously identified and characterized (Korn and Brown, *Cell* 15:1145-1156, 1978) for this purpose. RNAPIII is responsible for the transcription of non-coding RNAs, such as tRNAs, snRNAs and the 5S rRNA, which require no posttranscriptional modification. These were PCR amplified from genomic DNA and cloned using HindIII-EcoRI. For the human studies, the 5S rRNA promoter sequences were replaced with human U6 RNAPIII sequences, PCR amplified from the pSilencer 2.1 vector (Life Technologies) and cloned using HindIII-EcoRI. For this purpose any similarly identified sequence 5' of non-coding RNAs, such as tRNAs, snRNAs or 5S rRNAs from different species could be used. These can also be combined with known RNAPII enhancers or regulators to increase or refine expression. The promoter and termination sequences are shown below.

Fly 5S RNAPIII promoter DNA sequence
(SEQ ID NO: 9):
5'CAGTCTATTTCAGTCTATGGGCATAACTGAATATCAGAGTATAAG
GACACTGTTTAGCCCCTCGACTTTC Human U6 RNAPIII promoter sequence
(SEQ ID NO: 10):
5'CCCAGTGGAAAGACGCGCAGGCAAAACGCACCACGTGACGGAGCG
TGACCGCGCGCCGAGCGCGCGCCAAGGTCGGGCAGGAAGAGGGCCTA
TTTCCCATGATTCCTTCATATTTGCATATACGATACAAGGCTGTTAG
AGAGATAATTAGAATTAATTTGACTGTAAACACAAAGATATTAGTAC
AAAATACGTGACGTAGAAAGTAATAATTTCTTGGGTAGTTTGCAGTT
TTAAAATTATGTTTTAAAATGGACTATCATATGCTTACCGTAACTTG
AAAGTATTTCGATTTCTTGGGTTTATATATCTTGTGGAAAGGACGCG Fly 5S RNAPIII termination sequence
(SEQ ID NO: 11):
5'CGTCCACAACTTTTTGCTGCCTGCTGCCTGCTGCCTGCTGCC Mitochondrial Coding RNAs With ORF Sequences Mitochondrial-targeted coding RNAs are expressed using RNAP III initiation and termination sequences. RNAP III polymerase is known to terminate at a string of 4 or more T residues (Bogenhagen and Brown, *Cell* 24:261-270, 1981; Chu et al., *Nucleic Acids Res* 25:2077-2082, 1997; Ciliberto et al., *Curr Top Dev Biol* 18:59-88, 1983; Korn and Brown, *Cell* 15:1146-1156, 1978), therefore the gene has been coded to limit strings of Ts to 3. The ATP6 and GFP ORFs were synthesized such that the nucleotide sequence lacked four or more consecutive Ts (in DNA) and the mitochondrial-expressed proteins are otherwise wild type. Exploiting codon differences between the cytosol and mitochondria, the eGFP gene was engineered such that the tryptophan (W) codon at position 57 is changed from UGG (W in cytosol) to UGA (W in mitochondria but a STOP in cytosol). The eGFP$_{cytoSTOP}$ design ensures that the GFP fluorescence will only occur when translation occurs within mitochondria.

ATP6 ORF RNA sequence (SEQ ID NO: 12):
5'UUAAAUUCAAUAAAUUGAAAAUGAUAACAAAUUUAUUCUCUGUAUU
CGACCCCUUAGCUAUCUUUAAUUUCUCACUUAAUUGAUUAAGAACAUU
CUUAGGACUCUUAAUAAUUCCUAGGAUCUAUUGAUUAAUACCUUCUCG
UUACAAUAUUAUAUGAAAUUCAAUCUUAUUAACUCUUCAUAAAGAAUU
UAAAACUUUAUUAGGACCAUCAGGUCAUAAUGGAUCUACUUUCAUCUU
UAUUUCUUUAUUCUCAUUAAUCUUAUUUAAUAAUUUCAUAGGAUUAUU
UCCAUAUAUCUUUACAAGAACAAGACAUUUAACUUUAACUUUAUCUUU
AGCUUUACCUUUAUGAUUAUGUUUCAUAUUAUAUGGAUGAAUUAAUCA
UACACAACAUAUAUUUGCUCAUUUAGUUCCUCAAGGAACACCCGCUAU
UCUUAUACCUUUCAUAGUAUGUAUUGAAACUAUUAGAAAUAUUAUUCG
ACCUGGAACAUUAGCUGUUCGAUUAACUGCUAAUAUAAUUGCUGGACA
UUUAUUAUUAACUCUCUUAGGAAAUACAGGAUCUUCUAUAUCUUAUAU
AUUAAUAACAUUCUUAUUAAUAGCUCAAAUUGCUUUAUUAGUAUUAGA
AUCAGCUGUAGCUAUAAUUCAAUCUUAUGUGUUUGCUGUAUUAAGAAC
UUUAUAUUCUAGAGAAGUAAAUUAA ATP6 ORF DNA sequence (SEQ ID NO: 13):
5' TTAAATTCAATAAATTGAAAATGATAACAAATTTATTCTCTGTAT
TCGACCCCTTAGCTATCTTTAATTTCTCACTTAATTGATTAAGAACAT
TCTTAGGACTCTTAATAATTCCTAGGATCTATTGATTAATACCTTCTC
GTTACAATATTATATGAAATTCAATCTTATTAACTCTTCATAAAGAAT
TTAAAACTTTATTAGGACCATCAGGTCATAATGGATCTACTTTCATCT
TTATTTCTTTATTCTCATTAATCTTATTTAATAATTTCATAGGATTAT
TTCCATATATCTTTACAAGAACAAGACATTTAACTTTAACTTTATCTT
TAGCTTTACCTTTATGATTATGTTTCATATTATATGGATGAATTAATC
ATACACAACATATATTTGCTCATTTAGTTCCTCAAGGAACACCCGCTA
TTCTTATACCTTTCATAGTATGTATTGAAACTATTAGAAATATTATTC
GACCTGGAACATTAGCTGTTCGATTAACTGCTAATATAATTGCTGGAC
ATTTATTATTAACTCTCTTAGGAAATACAGGATCTTCTATATCTTATA
TATTAATAACATTCTTATTAATAGCTCAAATTGCTTTATTAGTATTAG
AATCAGCTGTAGCTATAATTCAATCTTATGTGTTTGCTGTATTAAGAA
CTTTATATTCTAGAGAAGTAAATTAA eGFP ORF RNA sequence (SEQ ID NO: 14):
5'UUAAAUUCAAUAAAUUGAAAAUGGUGAGCAAGGGCGAGGAGCUGUU
CACCGGUGUGGUGCCCAUCCUGGUCGAGCUGGACGGCGACGUAAACGG
CCACAAGUUCAGCGUGUCCGGCGAGGGCGAGGGCGAUGCCACCUACGG
CAAGCUGACCCUGAAGUUCAUCUGCACCACCGGCAAGCUGCCCGUGCC
CUGACCCACCCUCGUGACCACCCUGACCUACGGCGUGCAGUGCUUCAG
CCGCUACCCCGACCACAUGAAGCAGCACGACUUCUUCAAGUCCGCCAU
GCCCGAAGGCUACGUCCAGGAGCGCACCAUCUUCUUCAAGGACGACGG
CAACUACAAGACCCGCGCCGAGGUGAAGUUCGAGGGCGACACCCUGGU
GAACCGCAUCGAGCUGAAGGGCAUCGACUUCAAGGAGGACGGCAACAU
CCUGGGGCACAAGCUGGAGUACAACUACAACAGCCACAACGUCUAUAU
CAUGGCCGACAAGCAGAAGAACGGCAUCAAGGUGAACUUCAAGAUCCG
CCACAACAUCGAGGACGGCAGCGUGCAGCUCGCCGACCACUACCAGCA
GAACACCCCCAUCGGCGACGGCCCCGUGCUGCUGCCCGACAACCACUA
CCUGAGCACCCAGUCCGCCCUGAGCAAAGACCCCAACGAGAAGCGCGA
UCACAUGGUCCUGCUGGAGUUCGUGACCGCCGCCGGGAUCACUCUCGG
CAUGGACGAGCUGUACAAGUAA -continued
eGFP ORF DNA sequence (SEQ ID NO: 15):
5' TTAAATTCAATAAATTGAAAATGGTGAGCAAGGGCGAGGAGCTGTT
CACCGGTGTGGTGCCCATCCTGGTCGAGCTGGACGGCGACGTAAACGG
CCACAAGTTCAGCGTGTCCGGCGAGGGCGAGGGCGATGCCACCTACGG
CAAGCTGACCCTGAAGTTCATCTGCACCACCGGCAAGCTGCCCGTGCC
CTGACCCACCCTCGTGACCACCCTGACCTACGGCGTGCAGTGCTTCAG
CCGCTACCCCGACCACATGAAGCAGCACGACTTCTTCAAGTCCGCCAT
GCCCGAAGGCTACGTCCAGGAGCGCACCATCTTCTTCAAGGACGACGG
CAACTACAAGACCCGCGCCGAGGTGAAGTTCGAGGGCGACACCCTGGT
GAACCGCATCGAGCTGAAGGGCATCGACTTCAAGGAGGACGGCAACAT
CCTGGGGCACAAGCTGGAGTACAACTACAACAGCCACAACGTCTATAT
CATGGCCGACAAGCAGAAGAACGGCATCAAGGTGAACTTCAAGATCCG
CCACAACATCGAGGACGGCAGCGTGCAGCTCGCCGACCACTACCAGCA
GAACACCCCCATCGGCGACGGCCCCGTGCTGCTGCCCGACAACCACTA
CCTGAGCACCCAGTCCGCCCTGAGCAAAGACCCCAACGAGAAGCGCGA
TCACATGGTCCTGCTGGAGTTCGTGACCGCCGCCGGGATCACTCTCGG
CATGGACGAGCTGTACAAGTAA Example 2

Combining mtTRES Rescue and mtTRES TLI Vectors

This example describes the use of two mtTRES vectors—a first vector expressing a coding RNA for wild-type ATP6 (the rescue vector) and a second vector expressing a non-coding RNA that inhibits translation of mutant ATP6 (the translational inhibition (TLI) vector). The combination of the two vectors simultaneously inhibits translation of the mutant protein and provides wild-type protein to rescue the defect in ATP6.

In order for the rescue vector and the translational inhibition (TLI) vector to be combined most effectively, silent mutations were introduced into the ATP6 mtTRES rescue vector such that the ATP6 RNA would be resistant to translational inhibition by the TLI vector.

The TLIs are generated using the mtTRES vectors described in Example 1, with RNAPIII initiation and termination sites and NCLs to target the vectors to the mitochondria. Two TLIs were generated with 23-26 nucleotides of complementarity to the ATP6 translational initiation site. The complementary sequences of the TLIs are:

```
                                         (SEQ ID NO: 44)
    ATP6-TLI#1:     GAAAATAAATTTGTTATCATTTT (SEQ ID NO: 45)
    ATP6-TLI#2:     TACAGAAAATAAATTTGTTATCATTT
```

To generate an mtTRES-ATP6 that is resistant to TLIs (referred to as mtTRES-rATP6), changes were engineered into the translation initiation site to match the consensus sequence and silent changes were introduced into the coding region, as indicated below.

```
Endogenous ATP6     TTAAATTCAATAAATTGAAAATGATAACAAATTTATTTTCTGTA
SEQ ID NO: 48       (Protein-SEQ ID NO: 46) M  M  T  N  L  F  S  V mtTRES-ATP6         TTAAATTCAATAAATTGAAAATGATAACAAATTTATTCTCTGTA
SEQ ID NO: 49       (Protein-SEQ ID NO: 46) M  M  T  N  L  F  S  V Consensus           TTAAATTTWTAWWTTAATTA
                    (SEQ ID NO: 47)

mtTRES-rATP6        TTAAATTTATATATTAATTAATGATGACGAACCTGTTCAGCGTG
SEQ ID NO: 50       (Protein-SEQ ID NO: 46) M  M  T  N  L  F  S  V
```

The sequences for each construct include a translation initiation sequence, followed by a portion of the ATP6 coding region, which is translated below each coding sequence. The silent change introduced into the mtTRES-ATP6 and mtTRES-rATP6 sequences to avoid termination with RNAPIII transcription is in italics. The engineered changes in the mtTRES-rATP6 sequence to confer resistance to TLIs are underlined. All changes in the mtTRES-rATP construct are silent, as evidenced by the protein translation products shown below each coding sequence.

Example 3

In Vivo Functionality of mtTRES and TLI Vectors

This example demonstrates that the mtTRES and TLI vectors disclosed herein function in vivo.

Transgenic flies were made by embryonic injection using a standard site-directed phiC31 integration method (Bischof et al., *Proc Natl Acad Sci USA* 104(9):3312-3317, 2007). Germ line events resulting in transgenic flies were identified based upon eye color.

Transgenic *Drosophila* harboring mtTRES-NCL::eGFP were generated to evaluate whether the mtTRES RNAs are translated in vivo. Control animals transgenic for mtTRES lacking the GFP ORF (MRP Ctrl) were compared with *Drosophila* transgenic for mtTRES comprising the MRP and RNP NCLs (mtTRES-MRP::eGFP and mtTRES-RNP::eGFP, respectively). As shown in FIG. 1D, significant GFP fluorescence is detected in fly brains of mtTRES-MRP::eGFP and mtTRES-RNP::eGFP transgenic animals, that the GFP RNA is translated. Quantitation of the fluorescence images demonstrated that fluorescence in transgenic flies is well above the background fluorescence observed in control brains (FIG. 1E).

Figure 4A:
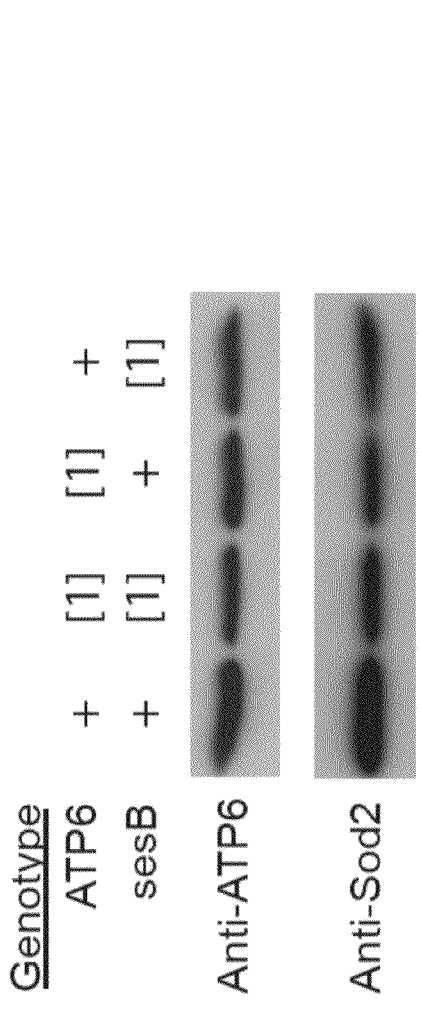
FIGS. 4A-4B show expression of mutant ATP6 protein in the fly.
Figure 4B:
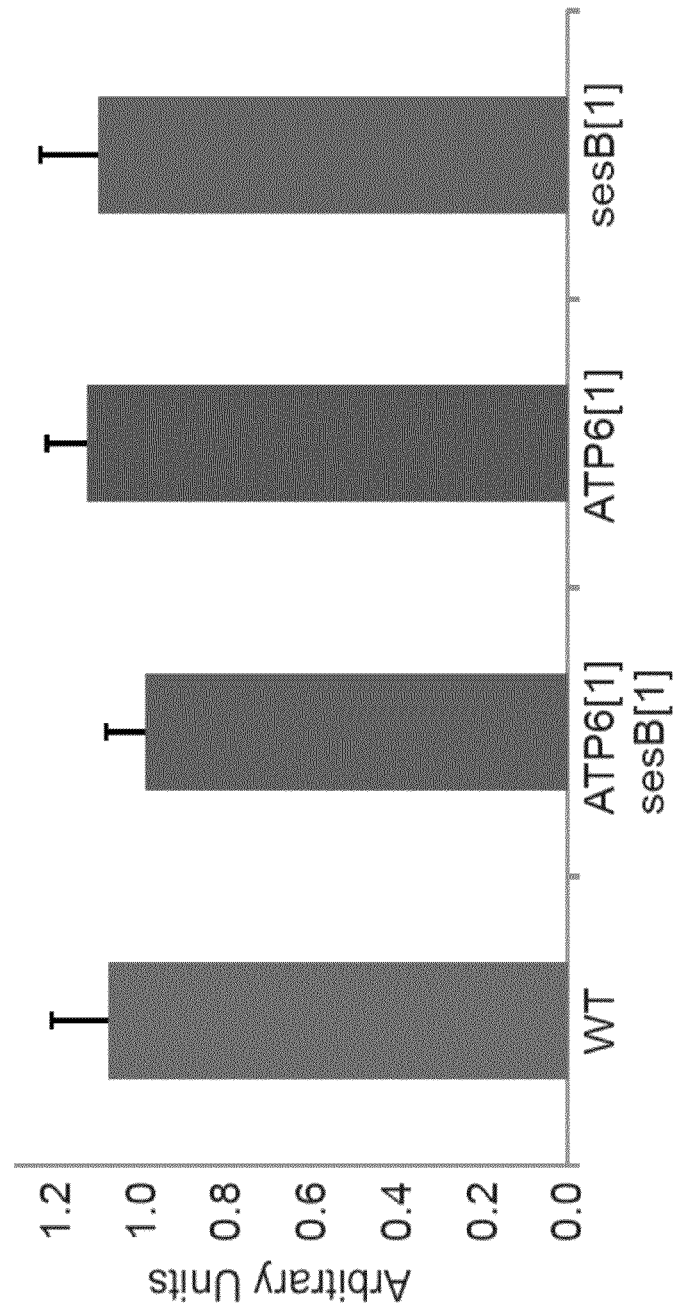

Additional studies were carried out to evaluate the expression of mutant ATP6 in ATP6 mutant (ATP6[1]) flies and whether expression of the mutant protein could be inhibited using a TLI vector. Western blot analysis demonstrated that the mutant ATP6 protein is expressed and exhibits unchanged steady state levels from controls (FIGS. 4A-4B). These data support the hypothesis that competition from the mutant protein represents a potential obstacle to the treatment of disease resulting from any of the numerous known mitochondrial protein coding missense mutations. There is tremendous therapeutic value of a mechanism capable of knocking down endogenous mitochondrial encoded protein levels.

Figure 5B:
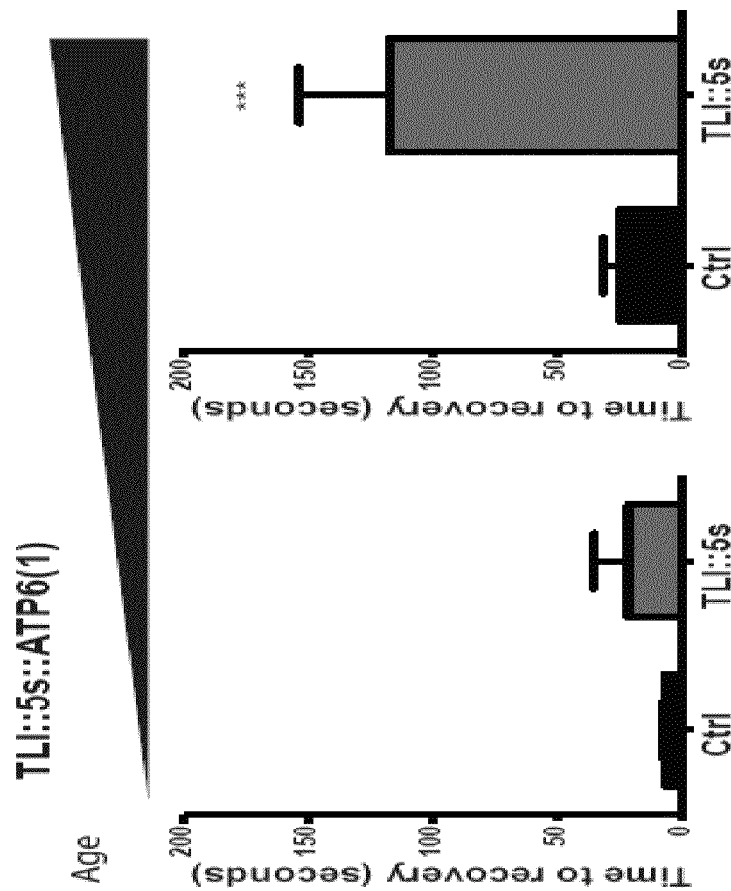
FIGS. 5A-5D demonstrate efficacious allotopic RNA therapy with translation inhibition (TLI) vector.
Figure 5A:
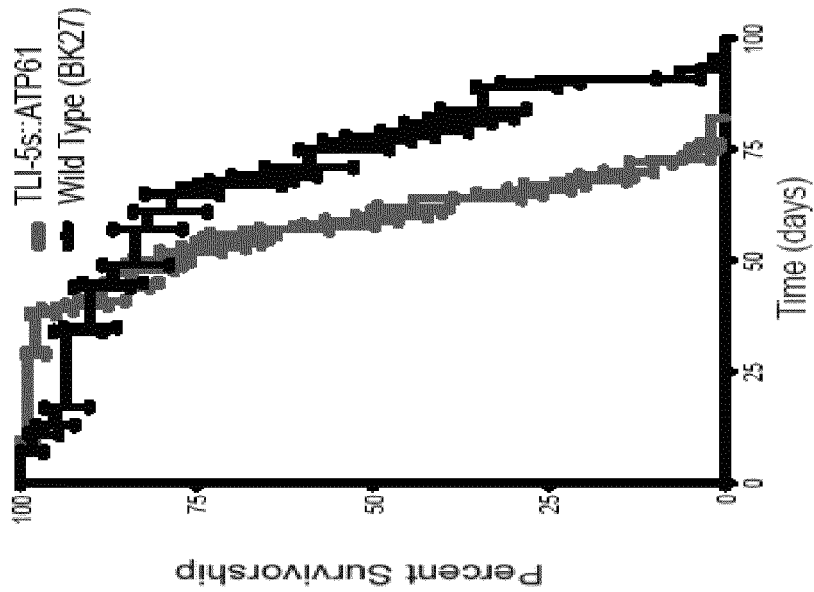

To evaluate whether a TLI vector is capable of inhibiting translation of ATP6 in vivo, TLI-5s::ATP6[1] transgenic flies were generated using a TLI vector comprising the 5s NCL and ATP6 TLI sequence (SEQ ID NO: 44) as described in Example 2. This study was carried out in transgenic flies that express wild-type ATP6 as a means to demonstrate that the ATP6 TLI is capable of inhibiting expression of ATP6. The ATP6 TLI is designed such that it will inhibit expression of both wild-type and mutant ATP6 protein. Survivorship of TLI-5s::ATP6[1] transgenic flies was compared with control flies. The results demonstrated that the ATP6 TLI reduces longevity (FIG. 5A) and causes a progressive loss in locomotor function (FIG. 5B) in vivo, which is similar to the ATP6[1] phenotype, demonstrating that translation of wild-type ATP6 is successfully inhibited in transgenic animals.

Figure 5C:
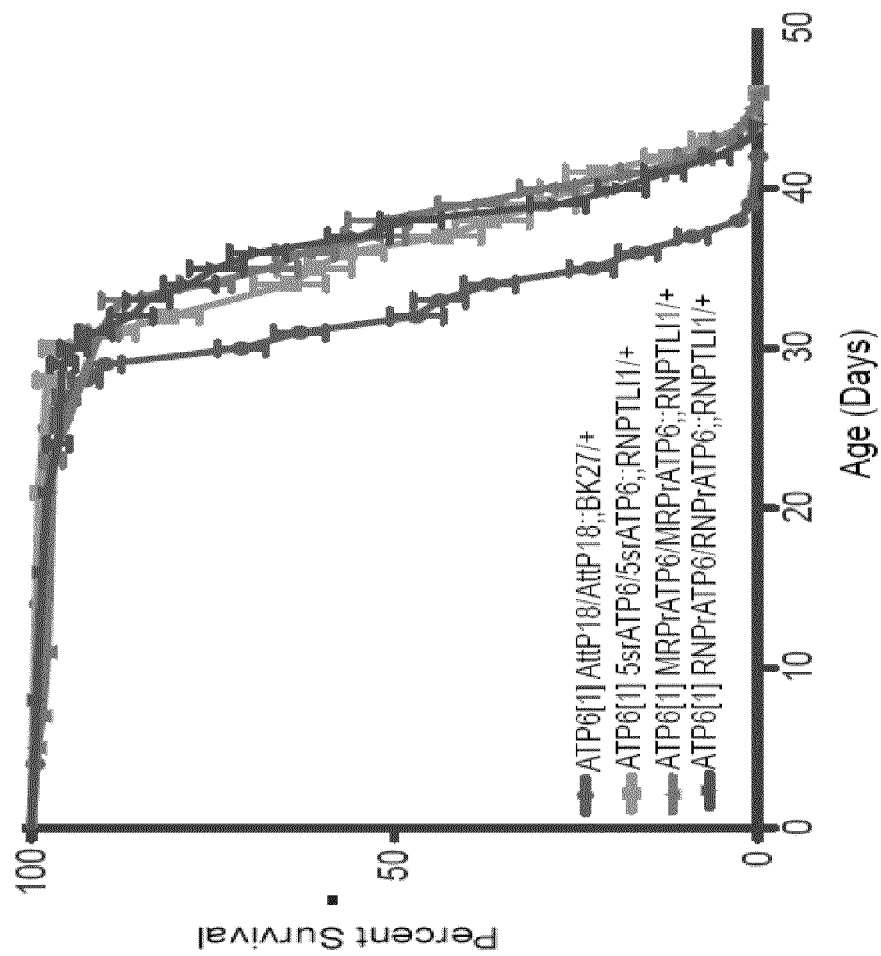
Figure 5D:
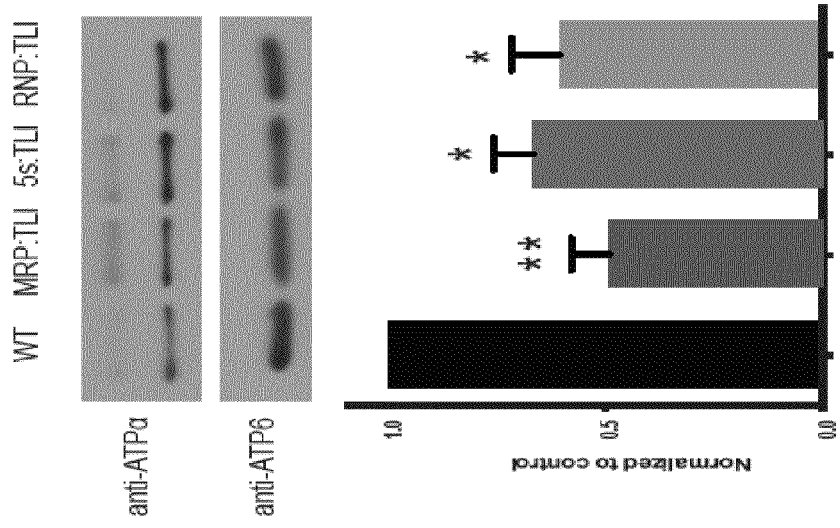

Next, three different ATP6 TLI vectors, each with a different NCL (MRP, 5s or RNP) were evaluated for their ability to inhibit ATP6 expression by Western blot (FIG. 5C). Quantitation of the Western blot demonstrated that ATP6 expression was reduced 35-50% (normalized to ATPα) resulting from ATP6 TLI. Thus, all three constructs with their independent NCLs were functional. To determine whether the decrease in survival observed in ATP6 TLI transgenic flies could be rescued, percent survival of *Drosophila* harboring one of three independent NCLrATP6 (modified with silent changes to be resistant to the TLI) vectors and the RNP:TLI to ATP6 was assessed (FIG. 5D). All three lines exhibited a clear and striking 20% increase in longevity. These data demonstrate with three independent NCLs that allotropic RNA expression is a viable therapy for mitochondrial coding gene mutations when combined with TLI.

Figure 6A:
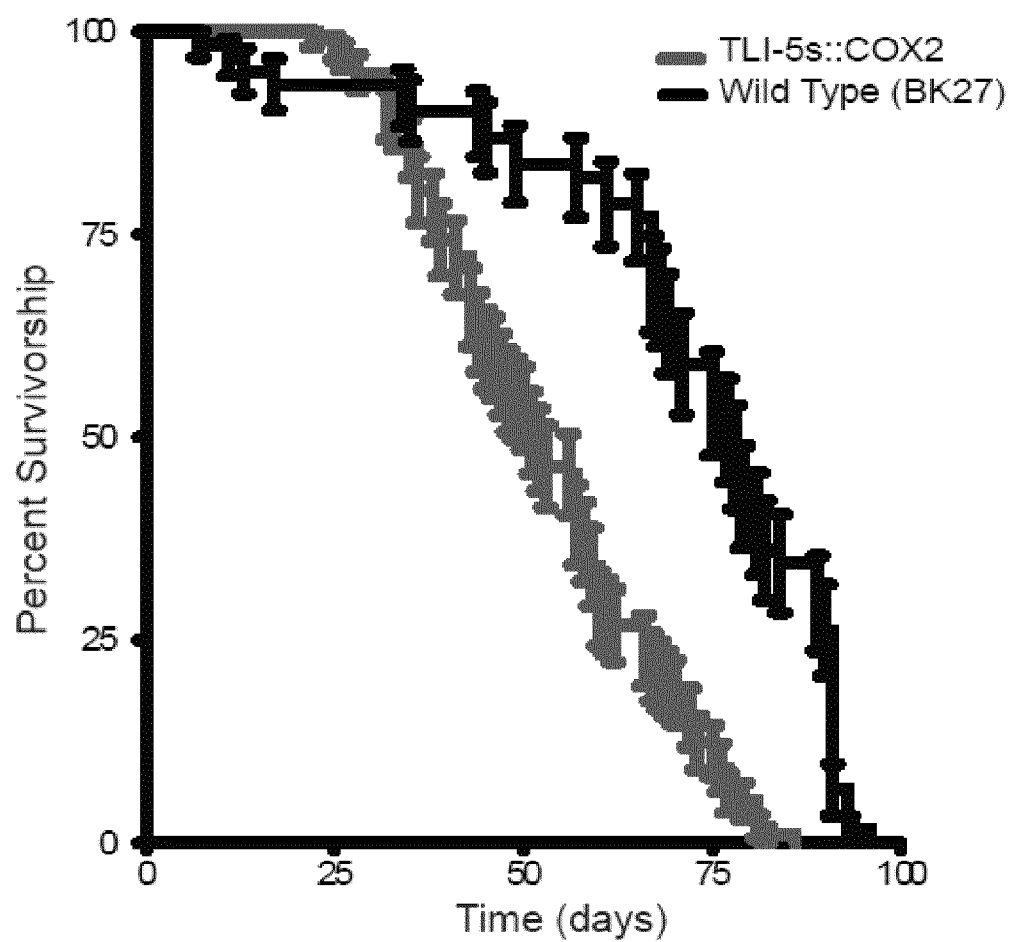
FIGS. 6A-6C show COXII TLIs are functional in vivo.
Figure 6B:
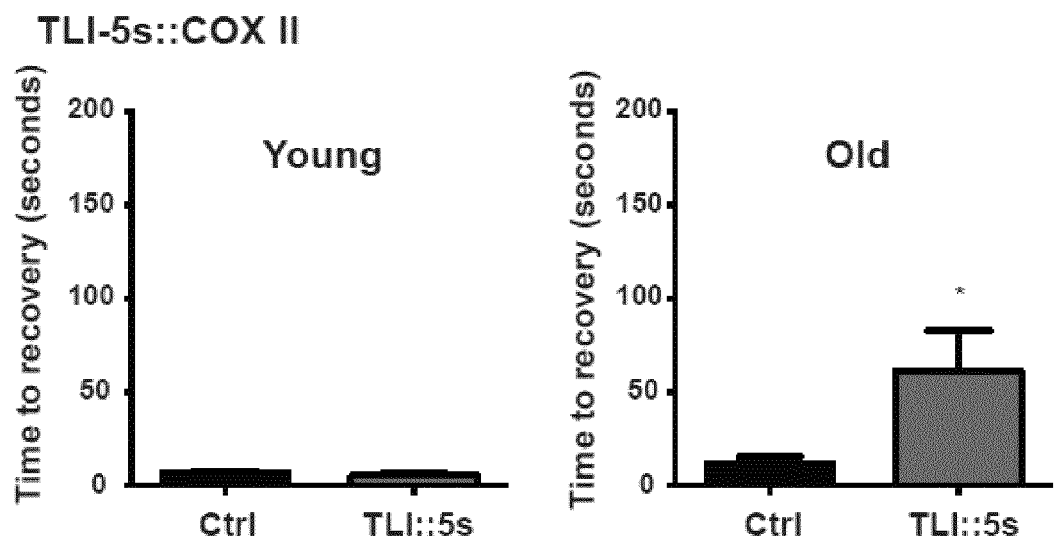
Figure 6B:
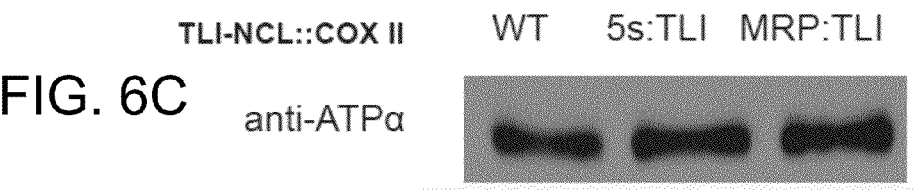
Figure 6C:
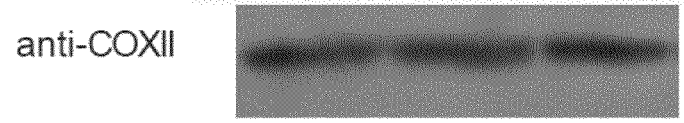
Figure 6C:
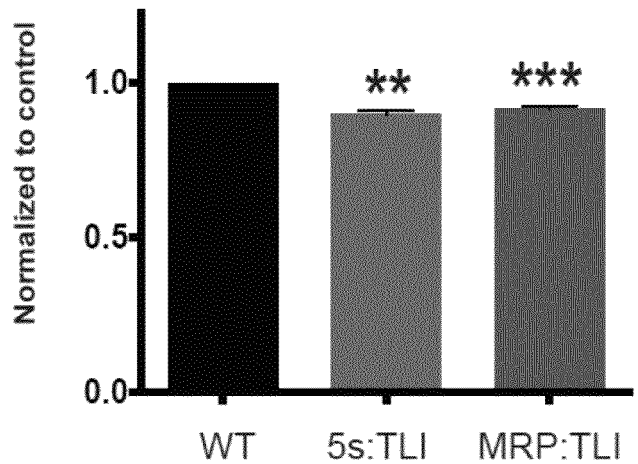

Similar results were obtained using a TLI to a second gene—COXII. TLI-5s::COXII transgenic *Drosophila* exhibited a significant decrease in survivorship (FIG. 6A) and locomotor function (FIG. 6B) compared to wild-type flies, demonstrating that the COXII TLI successfully inhibits expression of wild-type COXII in vivo. As shown in FIG. 6C, Western blot analysis demonstrated that expression of COXII was significantly reduced (10-15%) in *Drosophila* transgenic for either of two different COXII TLIs (5s:TLI or MRP:TLI).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. A vector comprising in the 5' to 3' direction:
an RNA polymerase III (RNAPIII) promoter sequence;
a non-coding mitochondrial leader sequence;
a mitochondrial translation initiation sequence and an open reading frame (ORF) encoding a protein, or a sequence encoding a non-coding RNA molecule capable of inhibiting translation of a mitochondrial mRNA molecule; and an RNAPIII termination sequence,
  wherein the RNAPIII promoter sequence is a 5S rRNA RNAPIII promoter sequence at least 95% identical to SEQ ID NO: 9.

2. The vector of claim 1, wherein the RNAPIII termination sequence is a 5S rRNA RNPAIII termination sequence.

3. The vector of claim 2, wherein the 5S rRNA RNPAIII termination sequence is at least 95% identical to SEQ ID NO: 11.

4. The vector of claim 1, wherein the non-coding mitochondrial leader sequence comprises a 5S rRNA leader sequence, an MRP leader sequence or an RNAse P leader sequence.

5. The vector of claim 4, wherein the 5S rRNA leader sequence is at least 95% identical to SEQ ID NO: 2, the MRP leader sequence is at least 95% identical to SEQ ID NO: 4, or the RNAse P leader sequence is at least 95% identical to SEQ ID NO: 6.

6. The vector of claim 1, wherein the mitochondrial translation initiation sequence comprises nucleotides 19-38 of any one of SEQ ID NOs: 16-29, nucleotides 11-30 of any one of SEQ ID NOs: 30-43, or SEQ ID NO: 8.

7. The vector of claim 1, wherein at least one codon of the ORF is modified such that the protein can be translated in the mitochondria but not in the cytosol.

8. The vector of claim 7, wherein the codon of the ORF is modified to contain a premature stop codon if translated in the cytosol and a tryptophan codon if translated in the mitochondria.

9. The vector of claim 1, wherein the ORF encodes a protein encoded by a mitochondrial gene.

10. The vector of claim 1, wherein the ORF encodes a reporter protein, and wherein at least one codon of the ORF is modified such that the reporter protein is translated in the mitochondria but not in the cytosol.

11. The vector of claim 1, wherein the vector encodes a non-coding RNA molecule that is capable of inhibiting translation of a mitochondrial mRNA molecule.

12. The vector of claim 11, wherein the non-coding RNA specifically hybridizes with a translation initiation site of the mRNA molecule.

13. An isolated host cell comprising the vector of claim 1.

14. A method of targeting a recombinant RNA molecule to the mitochondria of a cell, comprising contacting the cell with the vector of claim 1, wherein expression of the vector in the cell produces the recombinant RNA molecule which is targeted to the mitochondria.

15. A method of treating a disease caused by a mutation in a mitochondrial gene, comprising selecting a subject with a disease caused by the mutation in the mitochondrial gene and administering to the subject a therapeutically effective amount of at least one vector of claim 1.

16. The method of claim 15, wherein the subject is administered a first vector and a second vector, wherein the first vector comprises a mitochondrial translation initiation sequence and an ORF encoding a protein, and the second vector comprises a sequence encoding a non-coding RNA molecule capable of inhibiting translation of a mitochondrial mRNA molecule.

17. The method of claim 16, wherein the disease is caused by a mutation in the ATP6 gene, and wherein the ORF of the first vector encodes a wild-type ATP6 protein and the non-coding RNA molecule of the second vector inhibits translation of mutant ATP6 mRNA.

18. The method of claim 16, wherein the first vector comprises one or more silent mutations in the ORF such that translation of the protein is not inhibited by the non-coding RNA molecule of the second vector.

19. A vector comprising in the 5' to 3' direction:
  an RNA polymerase III (RNAPIII) promoter sequence;
  a non-coding mitochondrial leader sequence;
  a mitochondrial translation initiation sequence and an open reading frame (ORF) encoding a protein; and
  an RNAPIII termination sequence,
  wherein the RNAPIII promoter sequence is a 5S rRNA RNAPIII promoter sequence at least 95% identical to SEQ ID NO: 9.

20. A vector comprising in the 5' to 3' direction:
  an RNA polymerase III (RNAPIII) promoter sequence;
  a non-coding mitochondrial leader sequence;
  a mitochondrial translation initiation sequence and an open reading frame (ORF) encoding a protein, or a sequence encoding a non-coding RNA molecule capable of inhibiting translation of a mitochondrial mRNA molecule; and
  an RNAPIII termination sequence,
  wherein the 5S rRNA RNPAIII termination sequence is at least 95% identical to SEQ ID NO: 11.

21. A method of targeting a recombinant RNA molecule to the mitochondria of a cell, comprising contacting the cell with the vector of claim 20, wherein expression of the vector in the cell produces the recombinant RNA molecule which is targeted to the mitochondria.

* * * * *